United States Patent
Di Lauro et al.

(10) Patent No.: US 9,949,764 B2
(45) Date of Patent: Apr. 24, 2018

(54) SPINAL DEFORMITY CORRECTION

(71) Applicant: SeaSpine, Inc., Vista, CA (US)

(72) Inventors: Michael Di Lauro, Vista, CA (US); Nicholas M. Cordaro, Vista, CA (US); Raymund Woo, Vista, CA (US); Devin Mathios, Vista, CA (US)

(73) Assignee: SEASPINE, INC., Carlsbad, CA (US)

( * ) Notice: Subject to any disclaimer, the term of this patent is extended or adjusted under 35 U.S.C. 154(b) by 89 days.

(21) Appl. No.: 14/860,467

(22) Filed: Sep. 21, 2015

(65) Prior Publication Data
US 2016/0106472 A1    Apr. 21, 2016

Related U.S. Application Data

(63) Continuation of application No. 13/639,846, filed as application No. PCT/US2011/031267 on Apr. 5, 2011, now Pat. No. 9,138,261.
(Continued)

(51) Int. Cl.
*A61B 17/70*    (2006.01)
*A61B 17/86*    (2006.01)
(Continued)

(52) U.S. Cl.
CPC .......... *A61B 17/7032* (2013.01); *A61B 17/70* (2013.01); *A61B 17/708* (2013.01);
(Continued)

(58) Field of Classification Search
CPC .............. A61B 17/708; A61B 17/7079; A61B 17/7034; A61B 17/7037; A61B 17/7038
See application file for complete search history.

(56) References Cited

U.S. PATENT DOCUMENTS

| 5,005,562 A | 4/1991 | Cotrel |
| 5,330,474 A | 7/1994 | Lin |

(Continued)

FOREIGN PATENT DOCUMENTS

| WO | WO-03/032863 A2 | 4/2003 |
| WO | WO-2009/158707 A1 | 12/2009 |

OTHER PUBLICATIONS

Lonner, et al, "Thoracic Pedicle Screw Instrumentation," SPINE, vol. 34, No. 20, pp. 2158-2164 (2009).
(Continued)

*Primary Examiner* — Ellen C Hammond
(74) *Attorney, Agent, or Firm* — Middleton Reutlinger; Robert H. Eichenberger; Chad D. Bruggeman

(57) ABSTRACT

A spinal alignment system can include a rod and a plurality of uniplanar screw assemblies that include a screw, a cap, and a housing. The screw and cap can be configured such that the relative angular displacement between the screw and the cap is limited to a first limit angle in a first plane and to a second limit angle in a second plane that is perpendicular to the first plane, the second limit angle being larger than the first limit angle. The housing can be coupled to the cap and configured to maintain the cap in proximity with the head of the screw. The housing can have two elongated elements forming a U-shaped saddle. The alignment system can also include a plurality of locking cap assemblies that capture the rod within the U-shaped saddle and are tightened to fixedly couple the rod to the respective uniplanar screw assemblies.

28 Claims, 28 Drawing Sheets

Related U.S. Application Data

(60) Provisional application No. 61/321,250, filed on Apr. 6, 2010.

(51) Int. Cl.
*A61B 90/94* (2016.01)
*A61B 90/00* (2016.01)

(52) U.S. Cl.
CPC ...... *A61B 17/7011* (2013.01); *A61B 17/7035* (2013.01); *A61B 17/7038* (2013.01); *A61B 17/7083* (2013.01); *A61B 17/8605* (2013.01); *A61B 17/8615* (2013.01); *A61B 17/8665* (2013.01); *A61B 17/8685* (2013.01); *A61B 90/94* (2016.02); *A61B 17/7037* (2013.01); *A61B 2090/037* (2016.02); *A61B 2090/061* (2016.02)

(56) References Cited

U.S. PATENT DOCUMENTS

| | | | |
|---|---|---|---|
| 5,385,565 A | 1/1995 | Ray | |
| 5,520,690 A | 5/1996 | Errico et al. | |
| 5,669,911 A | 9/1997 | Errico et al. | |
| 5,752,957 A | 5/1998 | Ralph et al. | |
| 5,782,833 A | 7/1998 | Haider | |
| 5,814,046 A | 9/1998 | Hopf | |
| 5,882,350 A | 3/1999 | Ralph et al. | |
| 6,309,391 B1 | 10/2001 | Crandall et al. | |
| 6,485,494 B1 | 11/2002 | Haider | |
| 6,565,567 B1 | 5/2003 | Haider | |
| 6,689,137 B2 | 2/2004 | Reed | |
| 6,692,500 B2 | 2/2004 | Reed | |
| 6,733,502 B2 | 5/2004 | Altarac et al. | |
| 6,770,075 B2 | 8/2004 | Howland | |
| 6,800,078 B2 | 10/2004 | Reed | |
| 6,800,079 B2 | 10/2004 | Reed | |
| 7,081,117 B2 | 7/2006 | Bono et al. | |
| 7,314,467 B2 | 1/2008 | Howland | |
| 7,322,935 B2 | 1/2008 | Palmer et al. | |
| 7,322,979 B2 | 1/2008 | Crandall et al. | |
| 7,465,306 B2 | 12/2008 | Pond, Jr. et al. | |
| 7,655,008 B2 | 2/2010 | Lenke et al. | |
| 7,695,497 B2 | 4/2010 | Cordaro et al. | |
| 7,749,258 B2 * | 7/2010 | Biedermann | A61B 17/8605 606/266 |
| 7,766,944 B2 | 8/2010 | Metz-Stavenhagen | |
| 7,951,168 B2 | 5/2011 | Chao et al. | |
| 7,951,172 B2 | 5/2011 | Chao et al. | |
| 8,038,701 B2 | 10/2011 | Rock et al. | |
| 9,138,261 B2 | 9/2015 | Di Lauro et al. | |
| 2006/0122602 A1 | 6/2006 | Konieczynski et al. | |
| 2006/0149236 A1 | 7/2006 | Barry | |
| 2006/0155277 A1 | 7/2006 | Metz-Stavenhagen | |
| 2006/0195092 A1 | 8/2006 | Barry | |
| 2006/0200131 A1 | 9/2006 | Chao et al. | |
| 2006/0271050 A1 | 11/2006 | Piza Vallespir | |
| 2007/0093817 A1 | 4/2007 | Barrus et al. | |
| 2007/0162010 A1 | 7/2007 | Chao et al. | |
| 2007/0213715 A1 | 9/2007 | Bridwell et al. | |
| 2007/0213716 A1 | 9/2007 | Lenke et al. | |
| 2007/0270867 A1 | 11/2007 | Miller et al. | |
| 2008/0009864 A1 | 1/2008 | Forton et al. | |
| 2008/0015601 A1 * | 1/2008 | Castro | A61B 17/7086 606/86 R |
| 2008/0119852 A1 * | 5/2008 | Dalton | A61B 17/7032 606/86 R |
| 2008/0234759 A1 | 9/2008 | Marino | |
| 2008/0294206 A1 * | 11/2008 | Choi | A61B 17/708 606/86 A |
| 2008/0306547 A1 | 12/2008 | Klyce et al. | |
| 2009/0018593 A1 | 1/2009 | Barrus et al. | |
| 2009/0062914 A1 | 3/2009 | Marino | |
| 2009/0105716 A1 | 4/2009 | Barrus | |
| 2009/0105769 A1 | 4/2009 | Rock et al. | |
| 2009/0228051 A1 | 9/2009 | Kolb et al. | |

OTHER PUBLICATIONS

Lee, et al., "Direct Vetebral Rotation: A New Technique of Three-Dimensional Deformity Correction With Segmental Pedicle Screw Fixation in Adolescent Idiopathic Scoliosis," SPINE, vol. 29, No. 3, pp. 341-349 (2004).

* cited by examiner

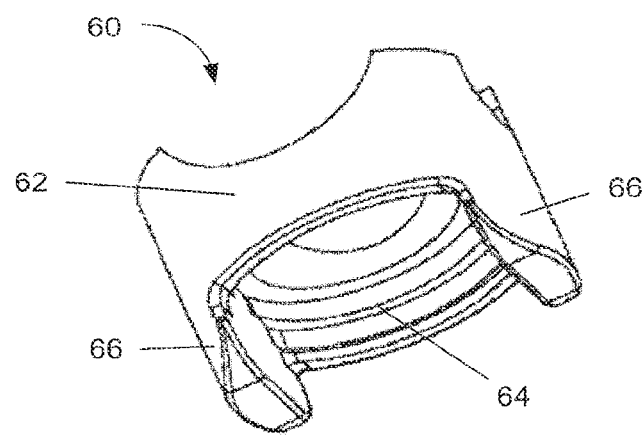
FIG. 5A
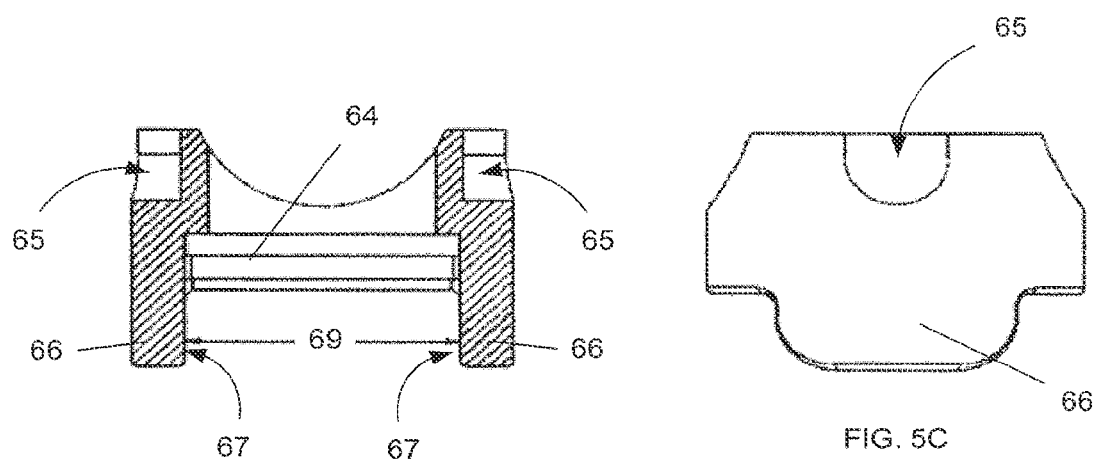
FIG. 5B
FIG. 5C

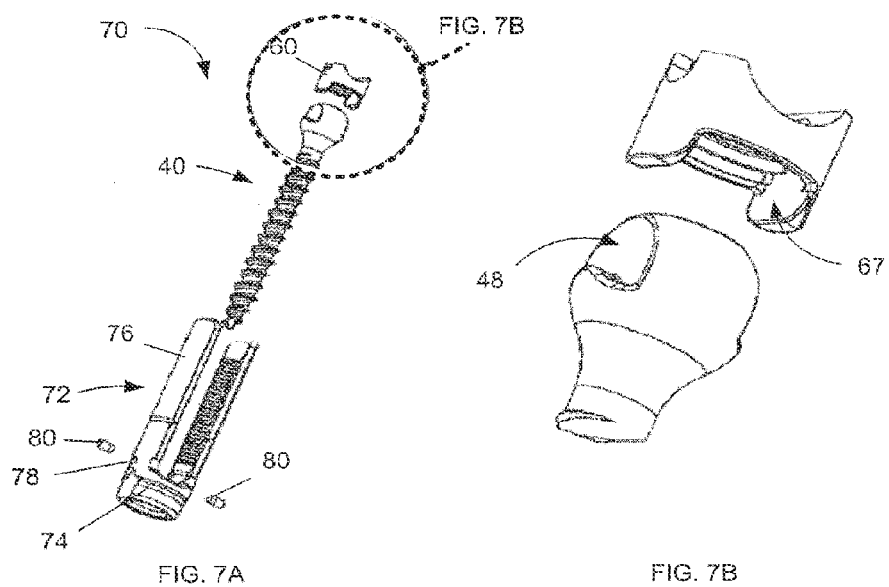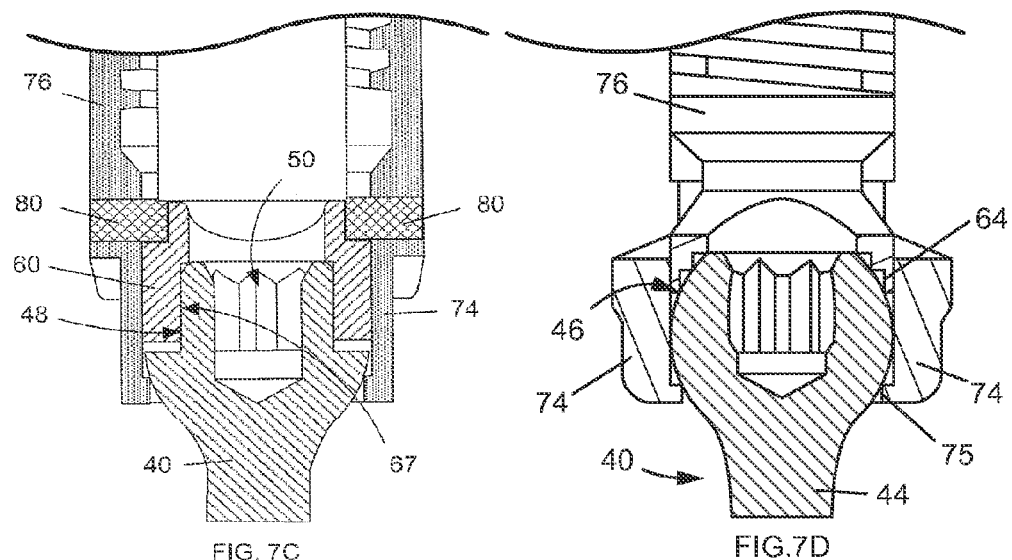

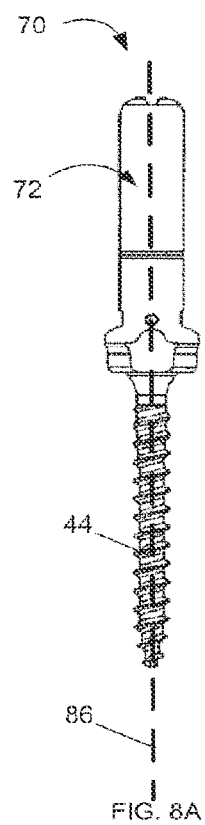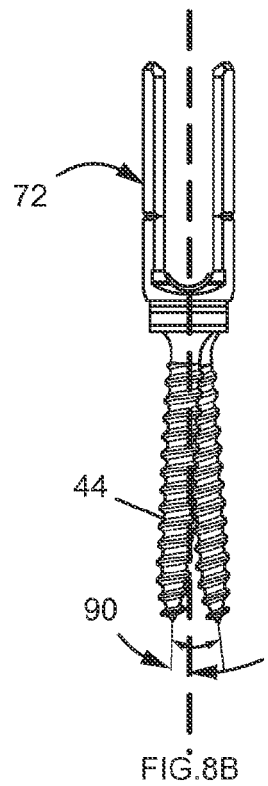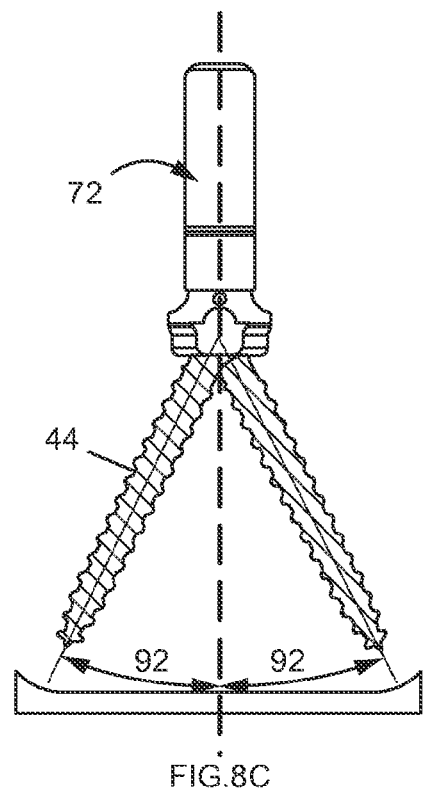
FIG. 8A  FIG. 8B  FIG. 8C
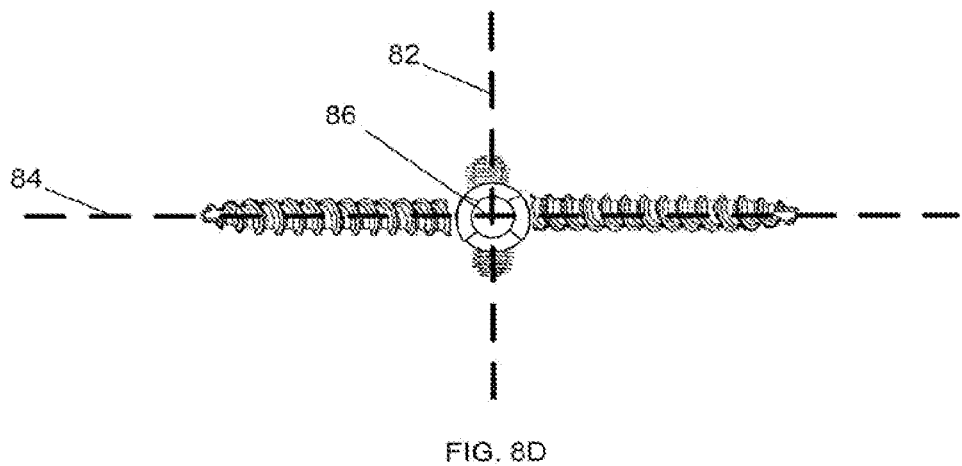
FIG. 8D

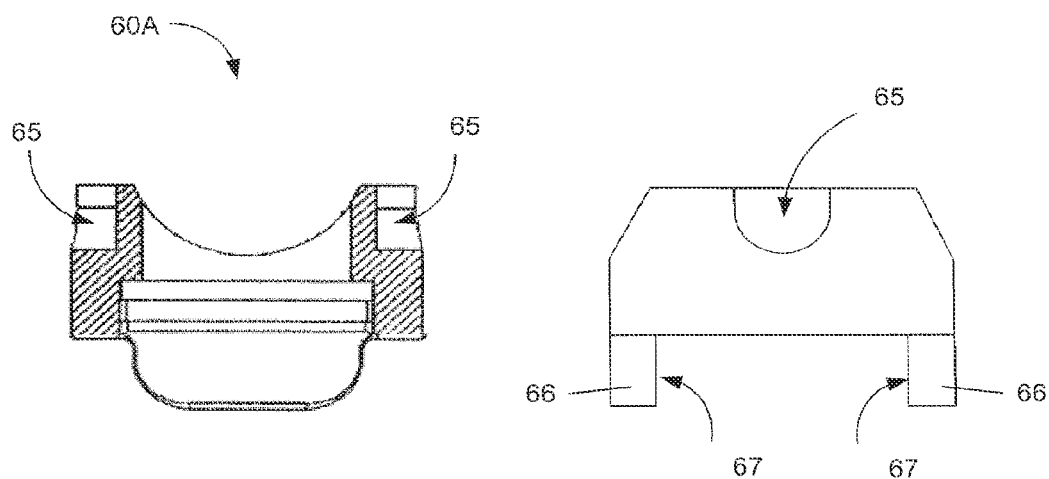

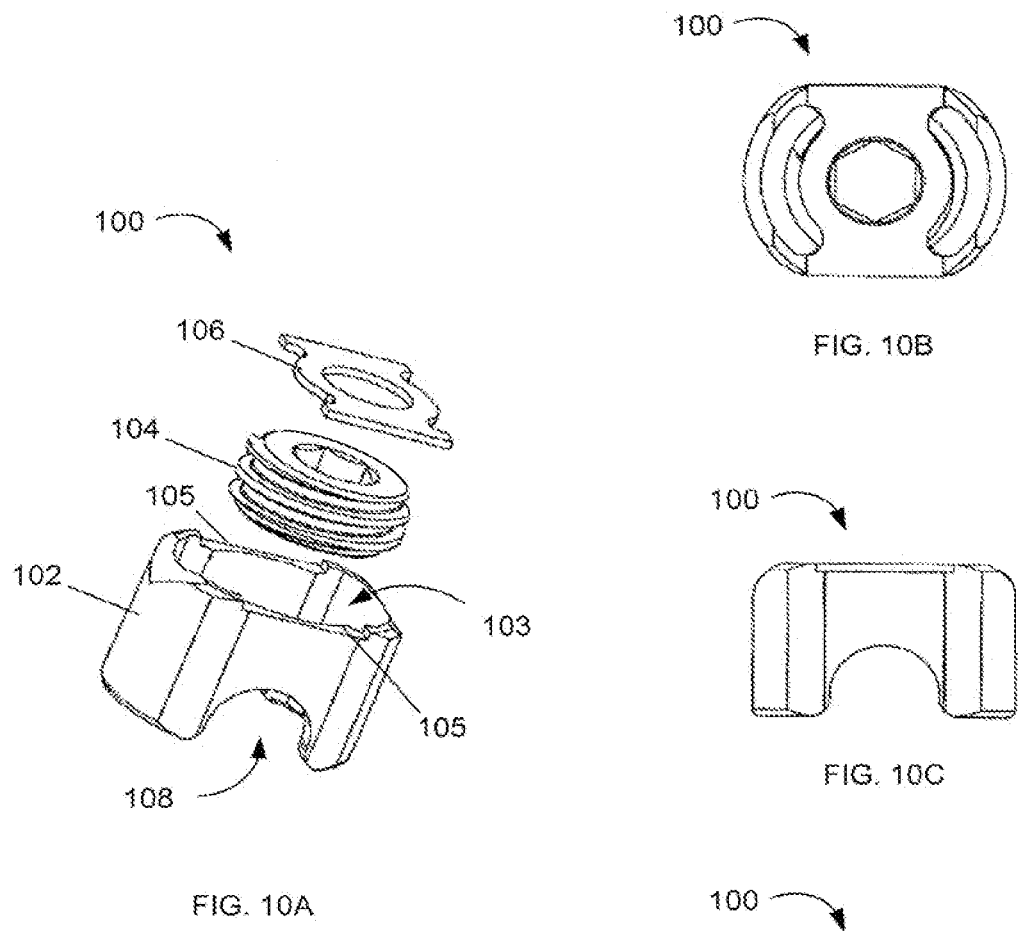

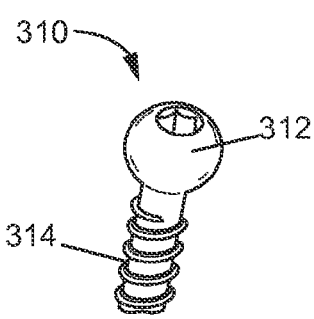
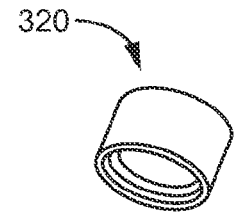
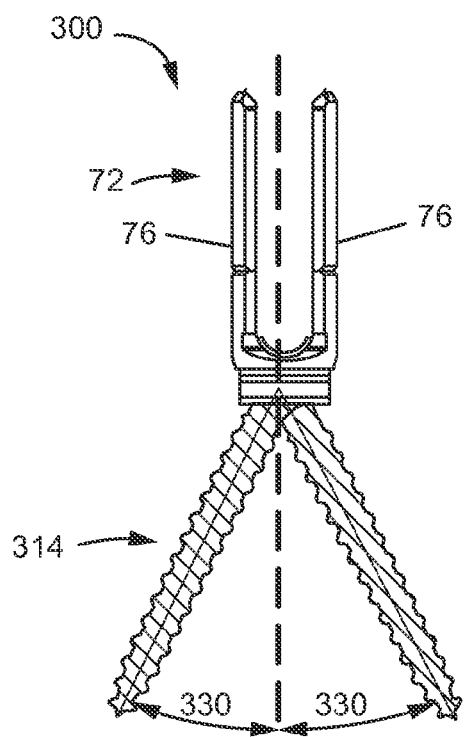
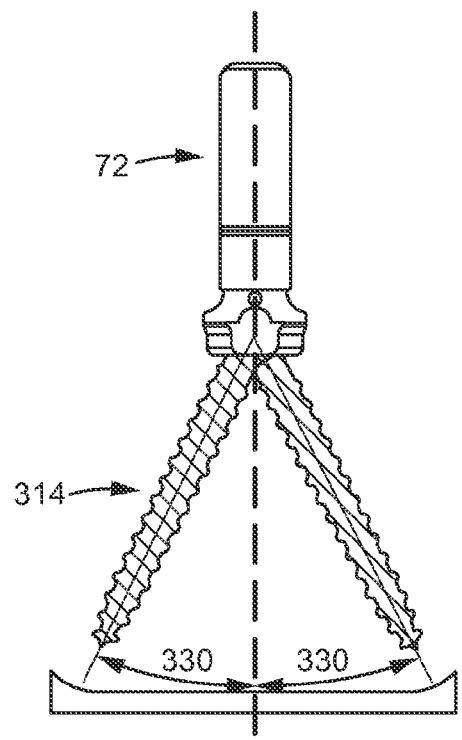
FIG.23A
FIG.23B
FIG.23C
FIG.23D

SPINAL DEFORMITY CORRECTION

CROSS-REFERENCE TO RELATED APPLICATIONS

This application is a continuation of U.S. patent application Ser. No. 13/639,846, filed on Dec. 21, 2012, which is the U.S. National Phase under 35 U.S.C. § 371 of International Application No. PCT/US2011/031267, filed on Apr. 5, 2011, which claims the benefit of U.S. Provisional Patent Application No. 61/321,250, filed on Apr. 6, 2010. The entire contents of each of these applications are herein incorporated by reference.

BACKGROUND

Field

The present disclosure generally relates to systems and methods for correcting spinal deformities.

Description of the Related Art

The treatment of spinal deformity requires a three dimensional approach and therefore is organized into three primary planes of correction relative to the human body. These three planes include the frontal or coronal plane, the sagittal or lateral plane, and the transverse or axial plane as shown in FIG. 1. Correction and proper alignment of these three planes is often the goal of the surgeon in the treatment of spinal deformity. Spinal deformities of varying etiologies are well known.

Over the past several decades, spinal fusion has been chosen as the standard of practice in the treatment of spinal deformity. Spinal fusion is the implantation of a rigid construct that may include rods, bone screws, hooks, and wires.

Early treatment of spinal deformity, more specifically scoliosis, involved a Harrington Rod developed by Dr. Paul Harrington. During this particular procedure, the Harrington rod is implanted along the spinal column to treat, among other conditions, a lateral or coronal plane curvature of the spine. With this procedure, no special attention was made to treat the sagittal or axial planes of alignment and as a result "Flatback Syndrome" developed whereby the spine progressively grew into an unnatural, straightened position with limited lordosis.

Years later, Dr. Yves Cotrel and Professor Jean Dubousset attempted to address all three aspects of planar management (i.e. Coronal, Sagittal and Axial) in the treatment of spinal deformity with the Cotrel-Dubousset (C-D) technique which was later modified by the Texas Scottish Rite Hospital (TSRH) in 1985. Both the C-D and the TSRH techniques required a curved rod and hooks as a spinal fusion construct. Furthermore, the C-D and TSRH technique required that a curved rod be rotated 90 degrees onto its side, utilizing the kyphosis and lordosis of the contoured rod to match the convexity and concavity of the spinal deformity. Once secured, the rod is then rotated to correct the coronal and sagittal balances of the spinal deformity. Subsequently, the C-D or TSRH technique failed to correct the axially unbalanced vertebra. As a result of the unaddressed axial balance, the patient is left with uneven shoulders or hips, also known as "Rotational Trunk Shift."

SUMMARY

In view of the shortcomings of the existing procedures for treating spinal deformities, there is a need for improvements which allow for the management of all three deformity planes in an effort to maximize a complete spinal deformity correction. It is desirable to not only manage all three deformity planes but allow for a de-rotation system to be assembled quickly with superior rigidity.

The disclosed system provides a method and system for correcting spinal deformities with special attention made for the coronal, sagittal, and axial planes. From an implant standpoint, uni-planar or monoaxial pedicle screws provide the surgeon with a rigid base by which the surgeon can cantilever against during the axial derotation maneuver. From an instrument standpoint, derotation tubes or restraint sleeves can be attached to either uniplanar or polyaxial screw assemblies to provide the surgeon with an extended element that can be controlled and manipulated during spinal derotation. Handles can be attached to the derotation tubes and restraint sleeves to provide further control and increased leverage to derotate the spine. Certain disclosed methods for derotating the spine using derotation tubes or restraint sleeves connect and control the derotation tubes and/or restraint sleeves as a single cluster in order to spread the concentration of forces involved with an axial correction. The disclosed system allows for a quick and rigid assembly of a derotation cluster.

In certain embodiments, a fastening system is disclosed that includes a screw having a head and a threaded portion that lies in both a first plane and a second plane that is perpendicular to the first plane. The fastening system also includes a cap configured to engage the head of the screw such that when the cap is engaged with the screw, the relative angular displacement between the threaded portion and the cap is limited to a first limit angle in the first plane and to a second limit angle in the second plane, the second limit angle being larger than the first limit angle.

In certain embodiments, a screw assembly is disclosed that includes a screw comprising a head and a threaded portion that lies in both a first plane and a second plane that is perpendicular to the first plane. The screw assembly also includes a cap configured to engage the head of the screw such that when the cap is engaged with the screw, the relative angular displacement between the threaded portion and the cap is limited to a first limit angle in the first plane and to a second limit angle in the second plane, the second limit angle being larger than the first limit angle, and a housing coupled to the cap, the housing configured to maintain the cap in proximity with the head of the screw.

In certain embodiments, an alignment system is disclosed that includes a first rod and a plurality of uniplanar screw assemblies that each comprise a uniplanar screw comprising a head and a threaded portion that lies in both a first plane and a second plane that is perpendicular to the first plane, a uniplanar cap configured to engage the head of the uniplanar screw such that when the uniplanar cap is engaged with the uniplanar screw, the relative angular displacement between the threaded portion and the uniplanar cap is limited to a first limit angle in the first plane and to a second limit angle in the second plane, the second limit angle being larger than the first limit angle, and a housing coupled to the uniplanar cap, the housing configured to maintain the uniplanar cap in proximity with the head of the uniplanar screw, the housing comprising two elongated elements forming a U shaped saddle that is configured to accept the first rod, at least one elongated element comprising threads on a portion of the surface facing the other elongated element. The alignment system also includes a plurality of locking cap assemblies. Each locking cap assembly comprises a sliding element configured to fit around both elongated elements and slide along the elongated elements and a threaded element disposed within the sliding element and configured to engage the threads of the at least one elongated element. The first rod is configured to engage the plurality of uniplanar screw assemblies by moving laterally into the U-shaped saddle of the housings of the uniplanar screw assemblies. The plurality of locking cap assemblies are configured to be coupled to the housing so as to capture the first rod within the U-shaped saddle of the housing and, when the threaded element of the locking cap assembly is actuated, to displace the first rod along the U shaped saddle until the first rod is in contact with a bottom of the U-shaped saddle and then fixedly couple the first rod to the respective uniplanar screw assemblies.

In certain embodiments, an alignment system is disclosed that includes a rod and a plurality of polyaxial screw assemblies, each comprising a polyaxial screw comprising a head and a threaded portion that lies in both a first plane and a second plane that is perpendicular to the first plane, a polyaxial cap configured to engage the head of the polyaxial screw such that when the polyaxial cap is engaged with the polyaxial screw, the relative angular displacement between the threaded portion and the polyaxial cap is at least limited to a first limit angle in both the first and second planes, and a housing coupled to the polyaxial cap, the housing configured to maintain the polyaxial cap in proximity with the head of the polyaxial screw, the housing comprising two elongated elements forming a U shaped saddle that is configured to accept the rod. At least one elongated element comprises threads on a portion of the surface facing the other elongated element. The alignment system also includes a plurality of locking cap assemblies. Each locking cap assembly comprises a sliding element configured to fit around both elongated elements and slide along the elongated elements and a threaded element disposed within the sliding element and configured to engage the threads of the at least one elongated element. The alignment system also includes a plurality of restraint sleeves that are configured to slidably couple to the housings of respective polyaxial screw assemblies and engage the rod and extend above the housings and a plurality of restraint shafts configured to engage a pocket on the head of the polyaxial screw thereby aligning the threaded portion of the polyaxial screw with the restraint shaft and secure the respective restraint sleeves to the respective housings. The rod is configured to engage the plurality of polyaxial screw assemblies by moving laterally into the U-shaped saddle of the housings of the polyaxial screw assemblies. The plurality of locking cap assemblies are configured to be coupled to the housing so as to capture the rod within the U-shaped saddle of the housing and, when the threaded element of the locking cap assembly is actuated, to displace the rod along the U shaped saddle until the rod is in contact with a bottom of the U-shaped saddle and then fixedly couple the rod to the respective polyaxial screw assemblies.

In certain embodiments, a method of en-bloc correction of spinal deformity of a patient is disclosed. The method comprises the step of attaching a plurality of first screw assemblies each comprising a housing having two elongated elements forming a U-shaped saddle wherein at least one elongated element comprises threads on a portion of the surface facing the other elongated element, a screw comprising a head and a threaded portion, and a cap configured to engage the head of the screw such that when the cap is engaged with the screw, the relative angular displacement between the threaded portion and the cap is limited to a first limit angle in a first plane and to a second limit angle in a second plane that is perpendicular to the first plane, the second limit angle being larger than the first limit angle, to a plurality of spinal vertebrae of the patient. The method also comprises the steps of placing a first rod transversely across the U-shaped saddles of a portion of the first screw assemblies, placing a plurality of locking screw assemblies having a sliding element configured to fit around both elongated elements and slide along the elongated elements and a threaded element disposed within the sliding element and configured to engage the threads of the at least one elongated element over the respective U-shaped saddles of the housings so as to capture the first rod within the U-shaped saddles of the housings, actuating the threaded element of the locking screw assemblies to displace the first rod along the respective U-shaped saddles until the first rod is in contact with a bottom of the U-shaped saddle, and tightening the threaded element of the locking screw assemblies to fixedly couple the respective first screw assemblies to the first rod.

In certain embodiments, a method of en-bloc correction of spinal deformity of a patient is disclosed. The method comprises the step of attaching a plurality of polyaxial screw assemblies each comprising a housing having two elongated elements forming a U shaped saddle wherein at least one elongated element comprises threads on a portion of the surface facing the other elongated element, a polyaxial screw comprising a head and a threaded portion that lies in both a first plane and a second plane that is perpendicular to the first plane, and a polyaxial cap configured to engage the head of the polyaxial screw such that when the polyaxial cap is engaged with the polyaxial screw, the relative angular displacement between the threaded portion of the polyaxial screw and the polyaxial cap is at least limited to a first limit angle in both the first and second planes, to a plurality of spinal vertebrae of the patient. The method also comprises the steps of placing a rod transversely across the U-shaped saddles of the housings of the polyaxial screw assemblies, and placing a plurality of locking screw assemblies having a sliding element configured to fit around both elongated elements and slide along the elongated elements and a threaded element disposed within the sliding element and configured to engage the threads of the at least one elongated element over the respective U shaped saddles of the housings of the polyaxial screw assemblies so as to capture the rod within the U shaped saddles of the housings. The method also comprises the steps of coupling a plurality of restraint sleeves to the housings of respective polyaxial screw assemblies, and actuating a plurality of restraint shafts to respectively engage a pocket on the head of the polyaxial screws thereby aligning the threaded portion of the polyaxial screws with the respective restraint shaft and secure the respective restraint sleeves to the respective housings. The method also comprises the steps of actuating the threaded elements of the locking screw assemblies to displace the rod along the respective U-shaped saddles of the housings of the polyaxial screw assemblies until the rod is in contact with a bottom of the U shaped saddles of the polyaxial screw assemblies, and tightening the threaded elements of the locking screw assemblies to fixedly couple the respective polyaxial screw assemblies to the rod.

In certain embodiments, a handle for a surgical tool is disclosed. The handle includes a body having a passage and a handle post that includes a coupler having an open cannula configured to engage the surgical tool and a shaft fixedly attached to the coupler, the shaft having a bore that passes into the open cannula of the coupler, the shaft also configured to pass through the passage of the body. The handle also includes a locking assembly that includes a locking nut and a locking nut post fixedly attached to the locking nut and configured to engage the bore of the handle post shaft. Rotating the locking nut relative to the handle post shaft advances the locking nut post through the bore of the handle post shaft and into the open cannula of the coupler to secure the handle to the surgical tool.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 5A-5C illustrate a cap according to certain embodiments of the present disclosure.

FIGS. 7A-7D are various views of a screw assembly according to certain embodiments of the present disclosure.

FIGS. 8A-8D depict the motion of a screw assembly according to certain embodiments of the present disclosure.

FIGS. 9A-9E illustrate another embodiment of a screw assembly according to certain embodiments of the present disclosure.

FIGS. 10A-10D are various views of a locking screw assembly according to certain embodiments of the present disclosure.

FIGS. 23A-23B are perspective views of a polyaxial screw and cap according to certain embodiments of the present disclosure.

FIGS. 23C-23D are front and side views of the polyaxial screw assembly according to certain embodiments of the present disclosure.

DETAILED DESCRIPTION

Figure 1:
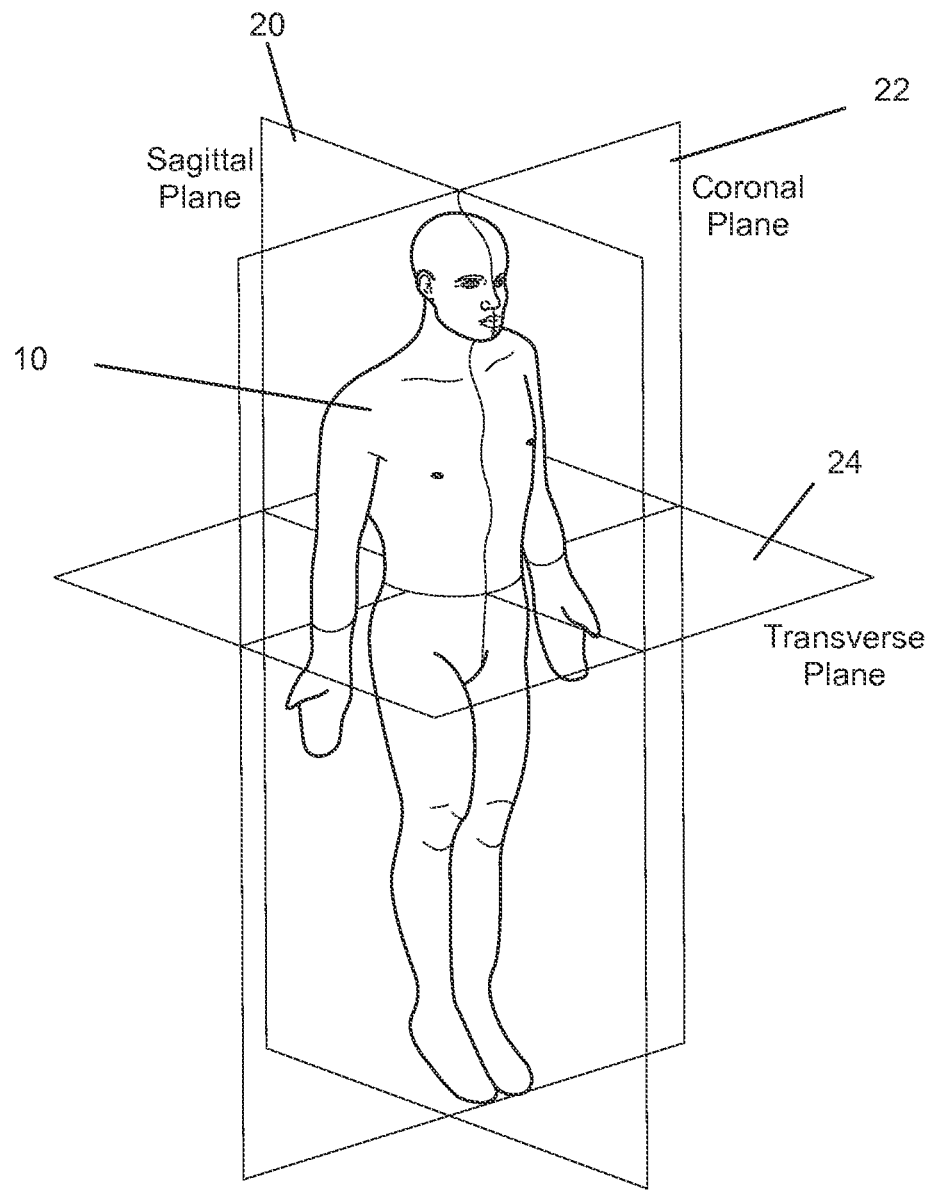
FIG. 1 is a diagram of the three reference planes of the human body.

The following description discloses embodiments of screw assemblies, derotation assemblies, lateral constructs, and derotation clusters that are to be used by surgeons to correct spinal deformity in the three primary planes of the human body. These various components and assemblies can be employed in multiple combinations and techniques depending on the condition of the patient and the preferences of the surgeon.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

For the purpose of the present disclosure, the term "derotation" refers to the method by which the axial or transverse balance of a deformity curve is restored.

For the purpose of the present disclosure, a "lateral construct" comprises, but is not limited to, rods, bone screws, and locking caps joined together for the purpose of fusing more than one vertebra together.

For the purpose of the present disclosure, the term "cluster" refers to a series of derotation tubes that are connected to one another both laterally and bi-laterally with respect to the fusion construct.

For the purpose of the present disclosure, the term "polyaxial" refers to the ability of one element, such as the threaded portion of a screw, to deflect a significant amount, i.e. greater than 10 degrees, in all directions relative to a coupled housing.

For the purpose of the present disclosure, the term "uniplanar" refers to the ability of one element, such as the threaded portion of a screw, to deflect a significant amount, i.e. greater than 10 degrees, in one plane relative to a coupled housing and a limited amount, i.e. less than 5 degrees, in a perpendicular plane.

For the purpose of the present disclosure, the term "monoaxial" and "uniaxial" refers to the ability of one element, such as the threaded portion of a screw, to not deflect relative to a second element, such as the coupled housing.

Certain embodiments of the present disclosure provide a lateral construct that is implanted on the posterior side of the patient for the treatment of spinal deformity. Certain embodiments of the lateral construct include screws that are rotatably coupled to elongated U-shaped housings to form screw assemblies. In certain embodiments, the threaded portion of the screw can move polyaxially with respect to the housing. In certain embodiments, the threaded portion of the screw articulates in a uni-planar motion. In certain embodiments, the uni-planar screw design is controlled by the interface between the screw housing and a cap whereby certain flats on the receiving end of the cap are paired with similar flats on the screw body.

In certain embodiments, the screws are implanted within the pedicles of selected vertebrae along the deformity curve of the spine. Once implanted, a rod is inserted into the U-shaped saddle of the screw assembly. The rod is secured to each of the implanted screws using a threaded locking screw assembly. In certain embodiments the elongated travel of the U-shaped saddle of the housing allows the surgeon to segmentally reduce the locking screw assembly in a controlled fashion.

In certain embodiments, the surgeon bends the rod in-situ to configure the sagittal balance. In certain embodiments, the surgeon uses a pre-contoured rod to achieve the sagittal balance of the deformity curve. Once the rod is reduced at each level by incrementally tightening the locking screw assemblies of the implanted screws, the coronal and sagittal balance of the scoliotic spine are restored.

In certain embodiments, the surgeon utilizes a rod on a single lateral side of the construct to gain sagittal, coronal, and axial alignment. In certain embodiments, the surgeon uses two rods, arranged bi-laterally, to gain sagittal, coronal, and axial correction.

Once the coronal and sagittal alignments have been achieved, the axial or transverse alignment is next to be addressed. In certain embodiments of the present invention, derotation tubes are anchored at the proximal end of the elongated bone screw housing through a threaded derotation tube retaining post. In certain embodiments, the derotation tubes have modular handles attached to them for added derotation leverage.

Once anchored, the derotation tubes are joined together on a lateral side of the construct using a retaining clip. In certain embodiments, the retaining clip is comprised of two arms that are rotatably coupled to one another. A latch or quick release mechanism is used to secure the arms of the retaining clip in the closed, clamped, position. In certain embodiments, the retaining clip includes a compressible core that functions to increase the grip strength when multiple derotation tubes are attached as one.

In certain embodiments, the derotation tubes are cylindrical with a knurled surface to increase the grip strength with the compressible core of the retaining clip. Certain embodiments of the derotation tube have multiple flat surfaces designed to decrease rotation and increase alignment during the placement of the retaining clip. Derotation tube locking nuts are threaded onto such embodiments of the derotation tubes and tightened onto the assembled retaining clip to limit rotation and translation amongst adjoining derotation tubes. In certain embodiments, the derotation tubes and derotation tube locking nuts have single or multi-lead threads. Translation and rotation of adjoining derotation tubes are avoided to maintain a rigid cluster; necessary to derotate the spine in restoring axial balance. In certain embodiments, the retaining clip is used to rigidly connect more than one of the derotation tubes into a rigid subset on a bi-lateral side of the construct. In other embodiments, the retaining clip is used to rigidly connect more than one of the derotation sleeve assemblies on a bi-lateral side of the construct.

In certain embodiments, a second retaining clip is connected transversely to rigidly connect both sides of the said bi-lateral construct to form a single rigid cluster. In certain embodiments, the single rigid cluster includes a bi-lateral construct comprised of derotation tubes and another bilateral construct comprised of derotation sleeve assemblies. In certain embodiments, the single rigid cluster includes two bi-lateral constructs both comprised of derotation tubes only.

In certain embodiments, the bi-lateral construct may only consist of derotation sleeves on one side of the construct and a captured rod on the opposite side of the construct by which derotation is performed uni-laterally rather than bi-laterally.

Once formed, the single rigid cluster acts as a rigid proximal connection whereby pure rotation about the proximal handles is translated into pure rotation about the distal construct.

In certain embodiments, derotation constitutes derotating one cluster relative to another cluster. In certain embodiments, one or more clusters are attached along the spinal deformity at different endpoints of the spine. Axial correction is gained whereby two clusters are derotated in the opposite direction of one another.

In certain embodiments, an elongated retaining clip or stabilization arm is used to hold the position of the derotated clusters while the screws are fully secured to the rod through the final tightening of the locking screw assemblies.

FIG. 1 is a diagram of the three reference planes of the human body 10. These three planes include the coronal, or frontal, plane 22, which passes from left to right through the body. The sagittal, or lateral, plane 20 passes from front to back. The transverse, or axial, plane passes horizontally, for a standing person, through the body.

Figure 2A:
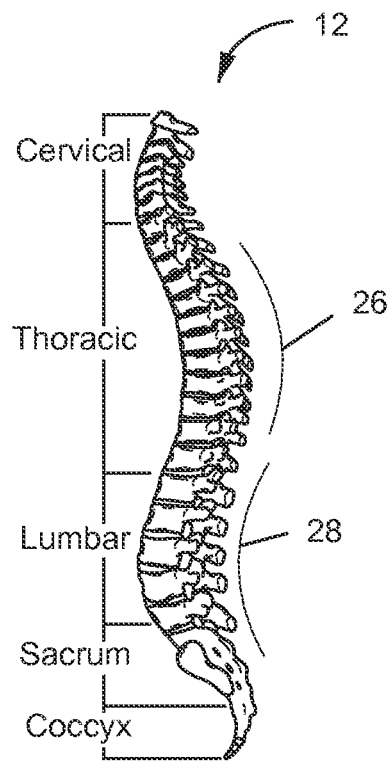
FIG. 2A is a lateral view of the spinal column and its regions.

FIG. 2A is a lateral view of the spinal column 12 and its regions. From the neck down, the spinal regions are the cervical region, the thoracic region, the lumbar region, the sacrum, and the coccyx. There are two types of curves in the spine: kyphosis (the spine curves inwards) and lordosis (the spine curves outwards). In a normal spine, the cervical and lumbar regions have a lordotic curve 28, while the thoracic region and sacrum have a kyphotic curve 26.

Figure 2B:
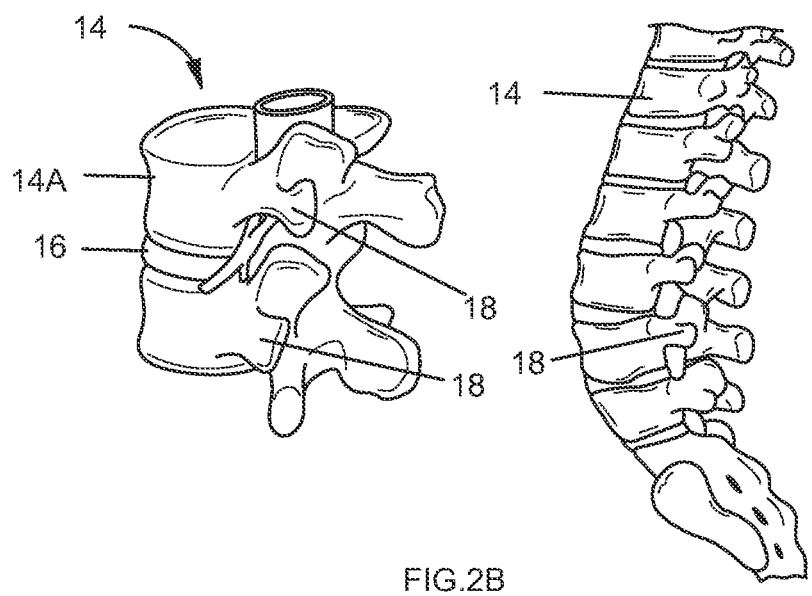
FIG. 2B illustrates the structure of an exemplary spine.

FIG. 2B illustrates the some of the structure of the spine. The spine includes a stacked series of vertebra 14 separated by discs 16. Many of the vertebrae 14 have flanges and protrusions, one of which is the pedicle 18 that is present on both sides of the vertebral body 14A.

Figure 3A:
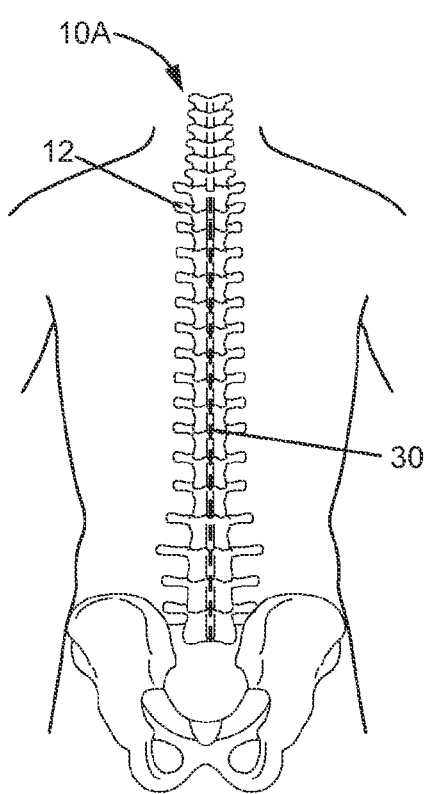
FIGS. 3A and 3B show a patient with a normal spine and a patient with scoliosis.
Figure 3B:
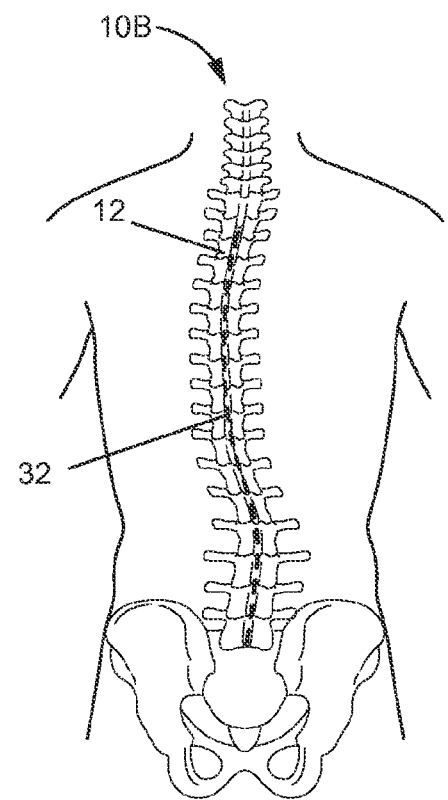

FIGS. 3A and 3B show a patient 10A with a normal spine and a patient 10B with scoliosis. As viewed from the back in FIG. 3A, the spine 12 of patient 10A follows a straight line 30 in the coronal plane 22. The spine 12 of patient 10B in FIG. 3B exhibits a double curve 32 in the coronal plane 22. Other patients may have curvature or offsets from the ideal spinal shape shown in FIG. 2A in the sagittal plane 20 or transverse plane 24.

Figure 4A:
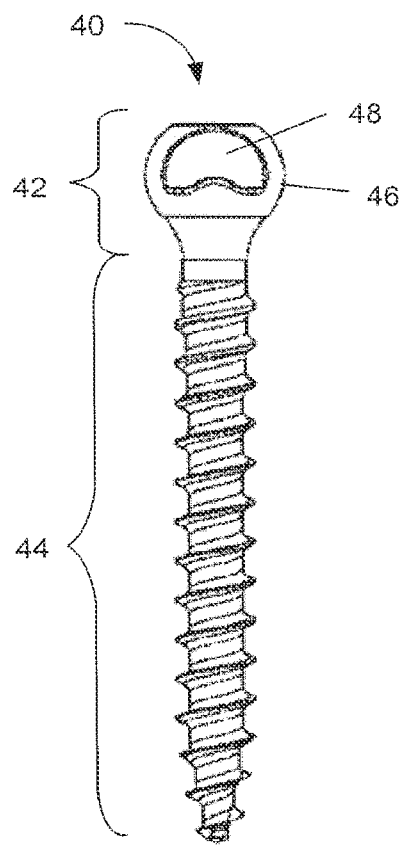
FIGS. 4A-4C illustrate a screw according to certain embodiments of the present disclosure.
Figure 4B:
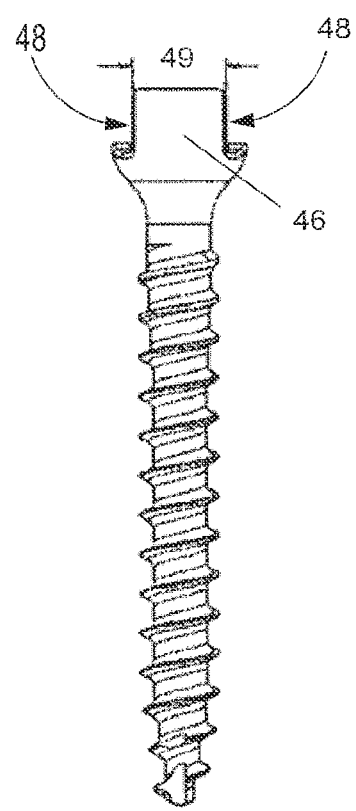
Figure 4C:
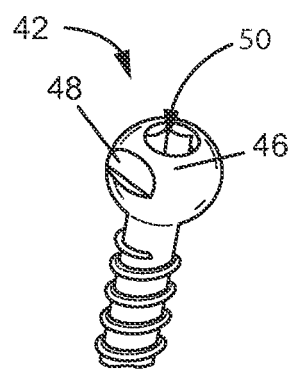

FIGS. 4A-4C illustrate a screw 40 according to certain embodiments of the present disclosure. Screw 40, also referred to as a bone screw or pedicle screw, has a head 42 and a threaded portion 44. FIGS. 4A and 4B are perpendicular lateral views of screw 40, while FIG. 4C is a perspective view of the head 42. The head 42 has a spherical surface 46 and a hexagonal pocket 50 suitable for receiving a hex-drive driver (not shown). The head 42 also includes, in this embodiment, a pair of flat surfaces 48 separated by a distance 49. As will be discussed in more detail with respect to FIGS. 7A-7C, these flat surfaces 48 are a part of the features that result in this particular embodiment being referred to as a uni-planar screw. The threaded portion 44 is, in this embodiment, configured with screw threads that are suitable for engagement with human spinal bone.

FIGS. 5A-5C illustrate a cap 60 according to certain embodiments of the present disclosure. FIG. 5A is a perspective view of cap 60, while FIG. 5B is a cross-section taken through the center of the cap 60 and FIG. 5C is a lateral external view of cap 60. The cap 60 has a body 62 with a central bore having a series of steps 64 that, as can be seen in FIG. 7D, are configured to engage the spherical surface 46 of the screw 40. Cap 60, in this embodiment, has two ears 66 that protrude below the body 62. Each ear 66 has a flat surface 67, with the two flat surfaces 67 separated by a distance 69. The body 62 also, in this embodiment, has a pair of blind notches 65 the function of which is described in more detail with regard to FIGS. 6A and 6C.

Figures 6A, 6B, 6C:
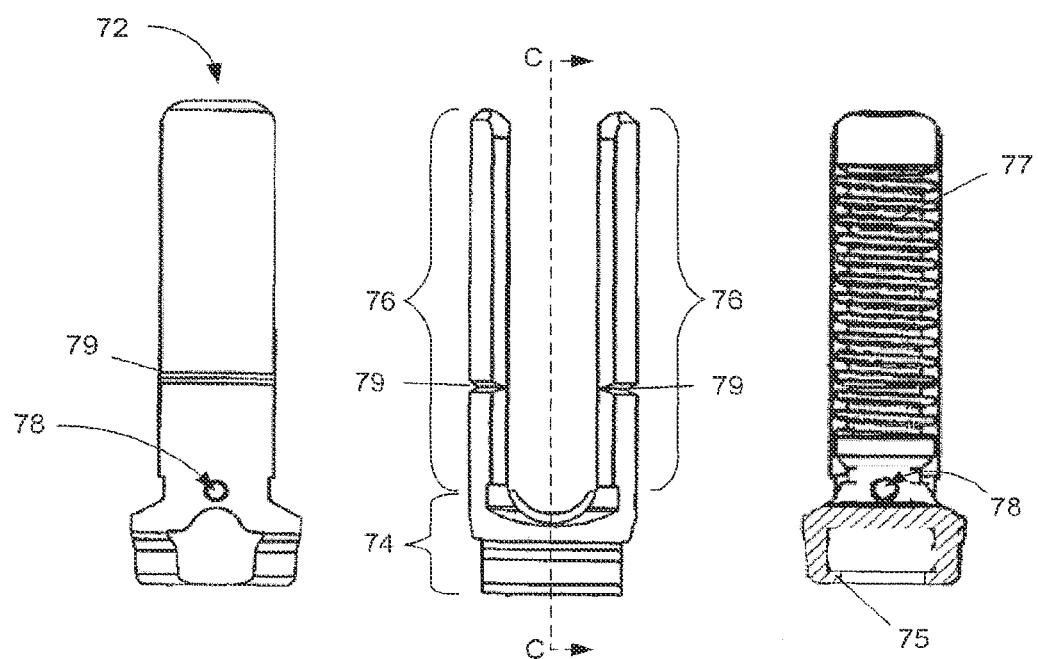
FIGS. 6A-6C are various views of a housing according to certain embodiments of the present disclosure.

FIGS. 6A-6C are various views of a housing according to certain embodiments of the present disclosure. FIGS. 6A and 6B are perpendicular lateral views of housing 72, while FIG. 6C is a cross-section of housing 72 taken along line C-C in FIG. 6B. The housing 72 has a base 74 with, in this embodiment, two elongated elements 76 that form a U-shaped saddle of the housing 72. The base 74 has a central vertical bore (not visible). A lip 75 is located at the lower edge of the bore, reducing the bore to a dimension that is less than the diameter of the head 42 of the screw 40. In this embodiment, the interior surface of each elongated element 76 has threads 77, as seen in FIG. 6C. There is a hole 78 penetrating through the housing 72 that is discussed in more detail with respect to FIGS. 7A and 7C. Each elongated element 76 has, in this embodiment, a groove 79 that will be discussed in more detail with respect to FIG. 11D.

FIGS. 7A-7D are various views of a screw assembly 70 according to certain embodiments of the present disclosure. FIG. 7A shows an exploded view of the components of screw assembly 70, including cap 60, screw 40, housing 72, and two pins 80. To assemble the screw assembly, the screw 40 is inserted between the elongated elements 76 and through the bore of the base 74 until the spherical surface 46 of screw 40 rests on the lip 75 of housing 70. The cap 60 is then placed over the head 42 within the bore of housing 70 and the two pins 80 are pressed into place in holes 78, thereby retaining the cap 60 in the housing 70 while allowing the screw 40 to rotate relative to the housing 70.

FIG. 7B is an enlarged view of the portion of FIG. 7A encircled by the broken-line circle 7B. When engaged as shown in FIG. 7A, the ears 66 of cap 60 are positioned such that, in this embodiment, the two surfaces 67 of the cap 60 are positioned adjacent to the two surfaces 48 of the screw 40.

FIG. 7C is a cross-section through the center of the assembled screw assembly 70, taken through the two pins 80. It can be seen how the pins 80 engage the blind holes 65 of the cap 60. In certain embodiments, pins 80 are press fit into the housing 72. In certain embodiments, an adhesive (not shown) is used to fix the pins 80 in housing 72. It is also visible herein how the surfaces 67 of cap 60 are aligned and adjacent to surfaces 48 of screw 40. The clearance between the surfaces 67 and surfaces 48 is controlled by the dimensions 49 and 69 of the screw 40 and cap 67, respectively. As will be discussed more fully with respect to FIGS. 8A-8D, a small amount of clearance allows a small amount of rotation of screw 40 with respect to cap 60 which is fixed, in an assembled screw assembly 70, relative to housing 72.

FIG. 7D is a cross-section through the center of the assembled screw assembly 70, taken at a right angle to the view of FIG. 7C. In this view, the spherical bearing formed by the combination of the steps 64 of cap 60 and the lip 75 of the housing 70 capturing the spherical surface 46 of screw 40. As the plane of the cross-section of FIG. 7D is parallel to the flat surfaces 48 and 67, screw 40 is allowed to rotate in the plane of the cross-section up to the point where the threaded portion 44 of the screw 40 contacts the base 74 of the housing 70.

FIGS. 8A-8D depict the motion of a screw assembly 70 according to certain embodiments of the present disclosure. FIG. 8A shows the screw assembly 70 in an "aligned" configuration, wherein both the housing 72 and the threaded portion 44 of screw 40 are coincident with an axis 86. FIG. 8D is a top view of screw assembly 70 that shows how axis 86 is formed by the intersection of mutually perpendicular first plane 82 and second plane 84.

FIG. 8B illustrates the range of motion of screw assembly 70 in first plane 82. As previously discussed with respect to FIG. 7C, the clearance between the flat surfaces 67 and flat surfaces 48 of the screw 40 and cap 60, respectively, allow angular displacement of screw 40 with respect to the housing 72 up to a first limit angle 90 in both directions away from the aligned position of FIG. 8A.

FIG. 8C illustrates the range of motion of screw assembly 70 in second plane 84 that is aligned with the flat surfaces 67 of cap 60 and, as a result of the pins 80, also with the elongated elements 76 of housing 72, respectively. Screw 40 can have an angular displacement with respect to the housing 72 up to a second limit angle 92 in both directions away from the aligned position of FIG. 8A.

FIG. 8D is a top view of screw assembly 70 showing the limits of angular displacement in first plane 82 and second plane 84 as well as the relation of axis 86 to mutually perpendicular planes 82 and 84.

Figure 9A:
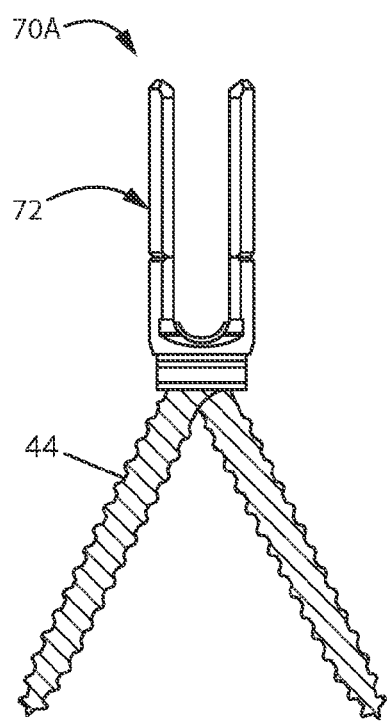
Figure 9B:
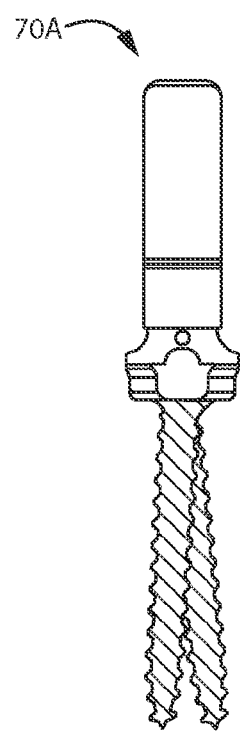
Figure 9C:
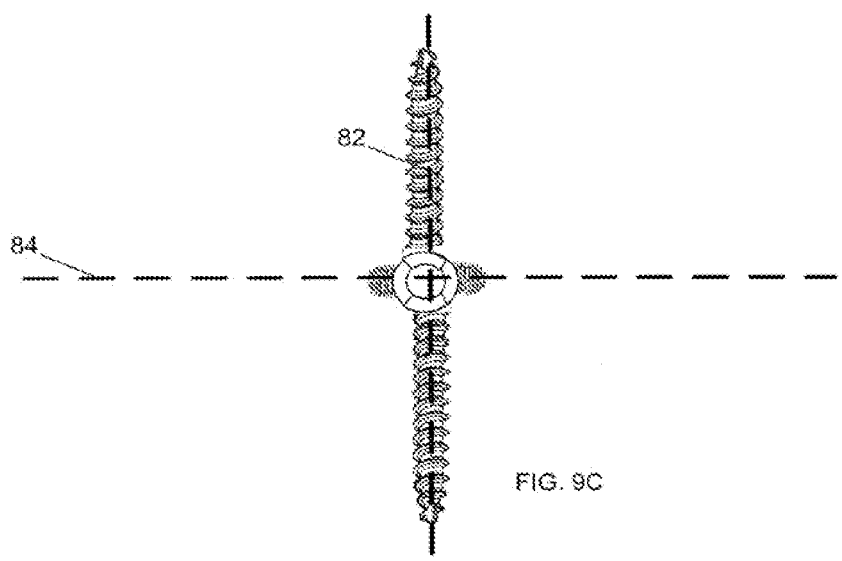

FIGS. 9A-9E illustrate another embodiment of a screw assembly 70A according to certain embodiments of the present disclosure. The screw assembly 70 of FIGS. 8A-8D had a large range of motion in plane 84, being parallel to the direction that a rod would pass through the U-shaped saddle of the housing 72, and a reduced range of motion in plane 82. FIGS. 9A and 9B are front and side views of a screw assembly 70A that has the large range of motion in plane 82 and a reduced range of motion in plane 84. This alternate configuration of ranges of motion is accomplished by cap 60A that is a modification of cap 60 of FIGS. 5A-5C, wherein the ears 66 are rotated by 90 degrees relative to the blind notches 65. When the screw assembly 70A is assembled, the ears 66 of cap 60A are located by the pins 80 to be perpendicular to the U-shaped saddle of housing 80, thereby rotating the large and reduced ranges of motion of screw assembly 70A by 90 degrees with respect to the screw assembly 70.

FIGS. 10A-10D are various views of a locking screw assembly 100 according to certain embodiments of the present disclosure. FIG. 10A is an exploded view of the components of locking screw assembly 100, including a sliding element 102 having an interior space 103 with a lip (not shown) at the bottom edge of the interior space 103. Sliding element 102 also has a pair of notches 108 the function of which will be discussed in more detail with respect to FIG. 10B. The locking screw assembly 100 also includes a threaded element 104 and a retention element 106. To assemble the locking screw assembly 100, the threaded element 104 is placed into the interior space 103, where the threaded element 104 rests on the lip, and retention element 106 is, in this embodiment, pressed into notches 105 on the two sides of interior space 103. In certain embodiments, the retention element 106 is bonded to sliding element 102. FIGS. 10B-10D are top, front, and bottom views, respectively, of locking screw assembly 100.

Figure 11A:
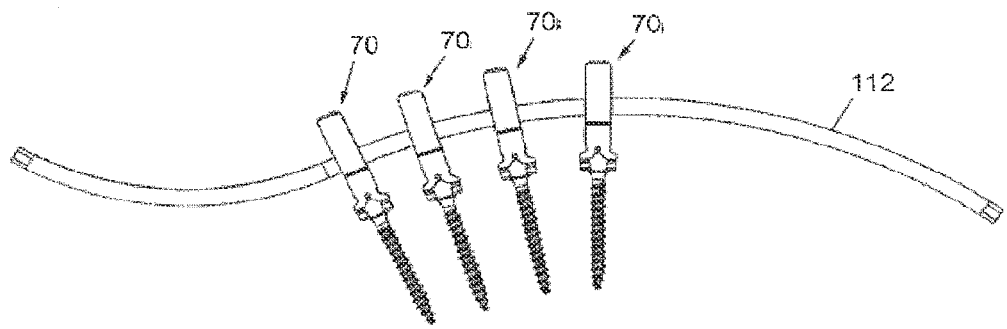
FIGS. 11A-11D depict the formation of an alignment system according to certain embodiments of the present disclosure.

FIGS. 11A-11D depict the formation of an alignment system 110 according to certain embodiments of the present disclosure. FIG. 11A is a front view of multiple screw assemblies 70 and a rod 112 whereby the rod 112 is located within the U-shaped saddle of the screw assemblies 70. In this embodiment, the rod 112 is pre-curved with lordotic curve 28 and a kyphotic curve 26 in the sagittal plane.

Figure 11B:
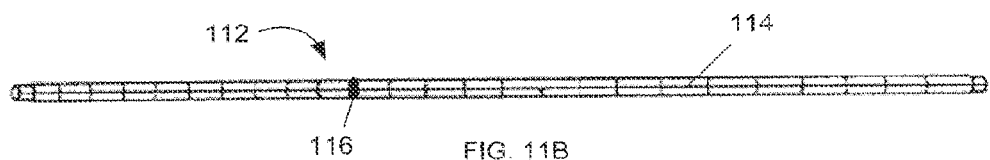
Figure 11C:
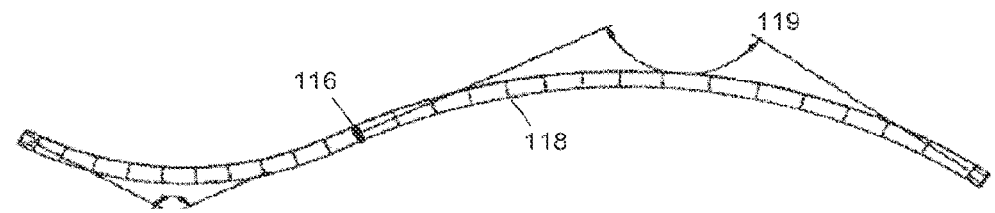

FIGS. 11B and 11C are top and side views, respectively, of a rod 112. FIG. 11B illustrates a rod 112 having a longitudinal line 114 scribed on one side to provide a reference for the orientation of the pre-bent rod 112. Being able to orient the rod 112 from the start of the surgery will give the surgeon an idea of the position of the spine and or the amount of correction needed to derotate the spine back to an anatomically correct position.

FIG. 11C shows how exemplary rod 112 is pre-bent, in this embodiment, into a 120 degree thoracic kyphotic curve 119 and a 125 degree lumbar lordotic curve 117. The rod 112, in this embodiment, has a transition indicator mark 116 that denotes the point of transition from the kyphotic curve 119 to the lordotic curve 117. This embodiment of rod 112 also has transverse indication marks 118, starting at the transition point and extending outward in both directions. Transverse indication marks 118 eliminate the need for the surgeon to manually measure the rod 112 based on measurements from a rod template (not shown) when cutting the rod 112. In certain embodiments, the transverse indication marks 118 are marked with serially numbered indicators (not shown). Since rods 112 are placed in the patient one at a time and cut to length during the surgery, transverse indication marks 118 with serially numbered indicators allow the second rod to be cut without additional measuring, thereby saving time and effort during the surgery. In certain embodiments, the numbering scheme of the serially numbered indicators is centered at the transition indicator mark 116. In certain embodiments, the serially numbered indicators increase in both directions away from the transition indicator mark 116.

Figure 11D:
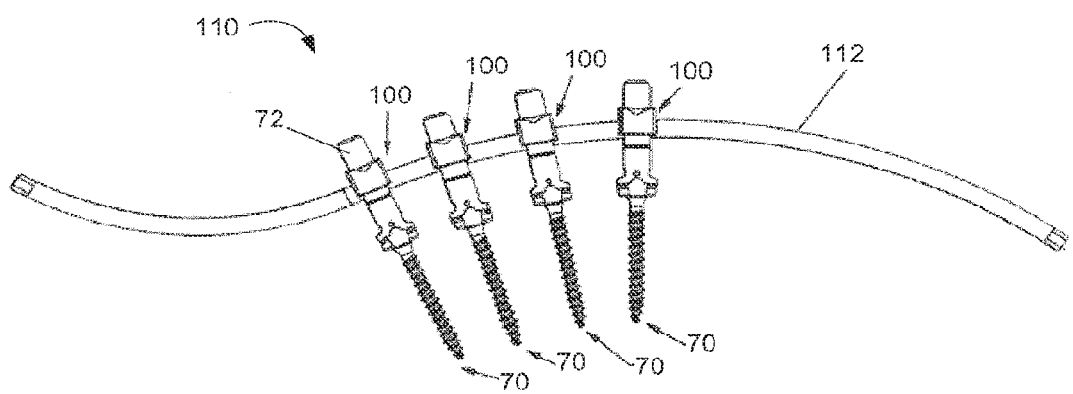

FIG. 11D shows the configuration of FIG. 11A with the addition of multiple locking cap assemblies 100 that are threadably coupled to the respective housings 72 of screw assemblies 70 by the threaded element 104 (not visible), forming an alignment system 110 that may be used to gain sagittal and coronal alignment for a patient.

After provisionally securing the rod in the screw assemblies 70 but before fully tightening the locking cap assemblies 100, the surgeon may rotate the rod using additional tools (not shown) until the desired correction is achieved in one or both of the coronal and sagittal planes. In certain embodiments, a surgeon may use two alignment systems 110, arranged bi-laterally on the spine, to gain sagittal and coronal correction. If no further manipulation is required, the locking cap assemblies 100 can be fully tightened to lock the housings 72 to the screw 40 in the current orientation, and the tops of the elongated elements 76 can be broken off at the grooves 79 shown in FIG. 6B.

Figure 12A:
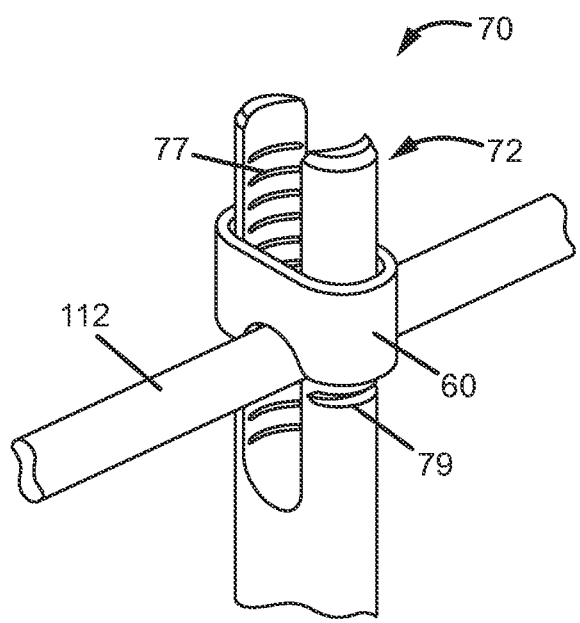
FIGS. 12A and 12B illustrate initial and final engagements of a cap with a screw assembly according to certain embodiments of the present disclosure.
Figure 12B:
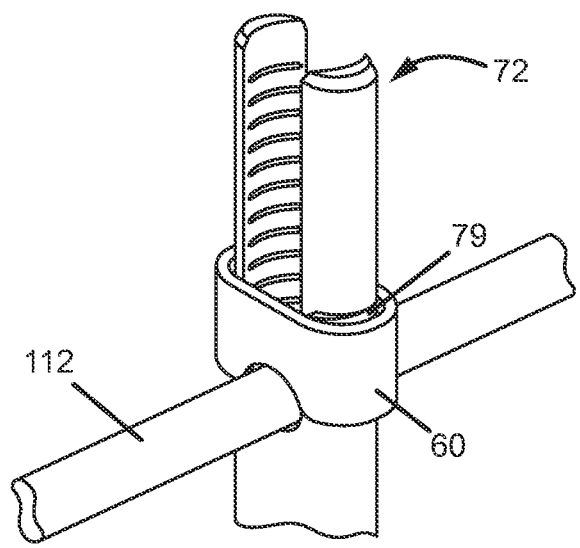

FIGS. 12A and 12B illustrate initial and final engagements of a locking cap assembly 100 with a screw assembly 70 according to certain embodiments of the present disclosure. In FIG. 12A, the rod 12 has been placed through the U-shaped saddle of screw assembly 70 at a mid-point of the height of the slot. A locking cap assembly 100 has been placed over the elongate elements of screw assembly 70 and the threaded element 104 (not visible) engaged with the threads 72 of the screw assembly 70. The threaded element 104 has been advanced until the sliding element 102 is in contact with the rod 112. After all of the screw assemblies 70 in a procedure have received a locking cap assembly 100, as shown in FIG. 11D, then the surgeon may incrementally advance the threaded elements 104 of all of the screw assemblies 70 to reduce the position of the rod 112 until it reaches the bottom of the U-shaped saddle, as shown in FIG. 12B. Once in this position, the threaded element 104 can be tightened, thereby engaging the steps 64 of the cap 60 with the spherical surface 46 of the screw 40 and locking the housing 72 and the screw 40 together in their present relative orientation.

Figure 13A:
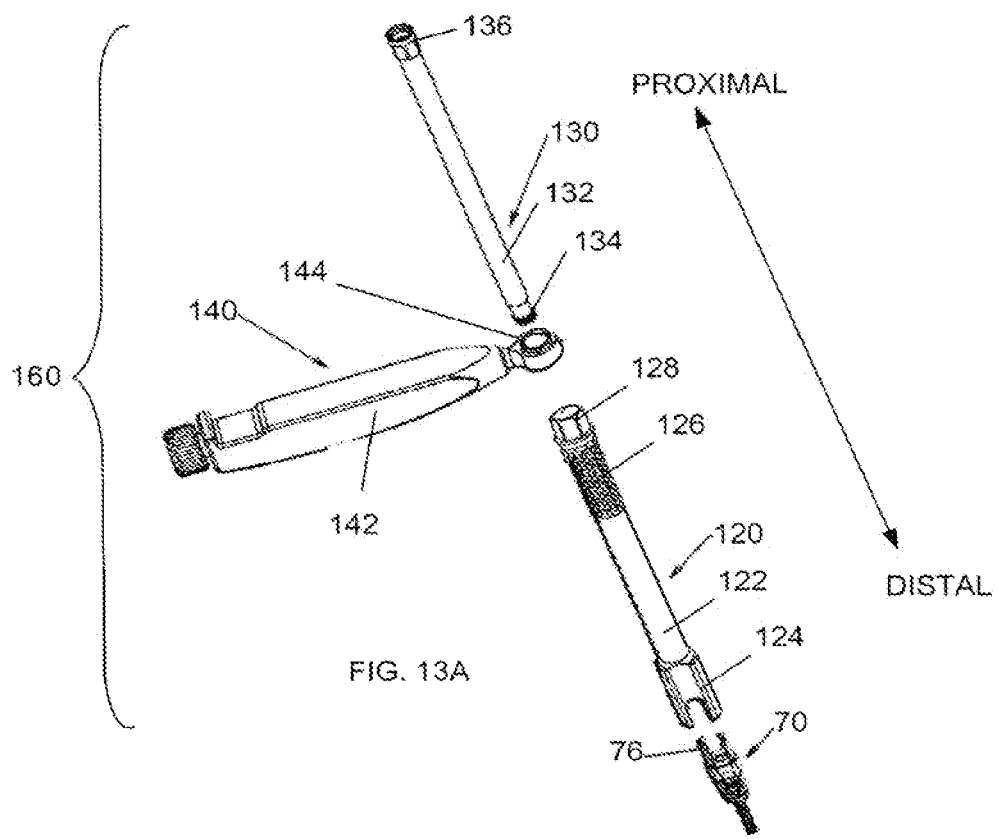
FIGS. 13A and 13B depict a derotation tube, a retaining post, and a handle according to certain embodiments of the present disclosure.
Figure 13B:
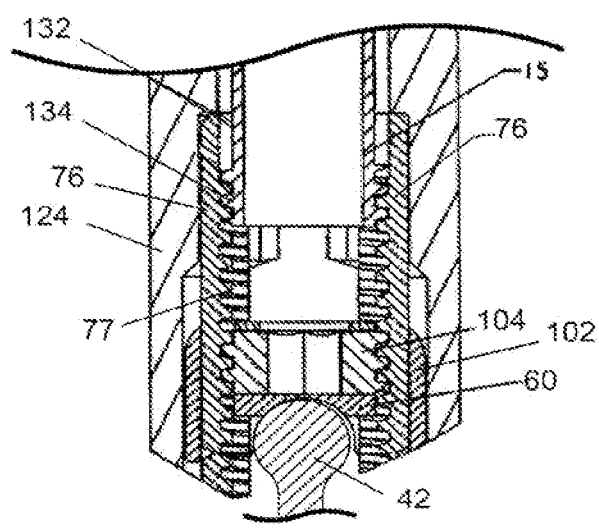

FIGS. 13A and 13B depict a derotation tube 120, a retaining post 130, and a handle 140 according to certain embodiments of the present disclosure. The derotation tube 120 has an engagement sleeve 124 at the distal end of a hollow tubular body 122. The engagement sleeve 124 is configured to slide over the proximal end of screw assembly 70 as is discussed in more detail with respect to FIG. 13B. The body 122 has, in this embodiment, a hexagonal feature 128 at its proximal end with a knurled surface 126 adjacent. The function of the knurled surface 126 is discussed in more detail with respect to FIG. 17A. Together, the derotation tube 120, a retaining post 130, and a handle 140 form a derotation tube assembly 160.

Retaining post 130 has a body 132 with a threaded tip 134 at the distal end. The body 132 also has a hexagonal feature 136 at the proximal end. The body 132 and threaded tip 134 are sized such that they fit through the interior bore of derotation tube 120.

Handle 140 has a body 142 connected to a hexagonal tip 142 that is configured to engage the hexagonal feature 128 of the derotation tube 120. The construction of the handle 140 is described in more detail with respect to FIG. 14.

FIG. 13B is an enlarged cross-section of the engagement sleeve 124 in place over the elongated elements 76 of screw assembly 70. Threaded element 104 can be seen to be in contact with cap 60 over the screw head 42, with the sliding element 102 around the outside of the elongate elements 76. The body 132 of the retaining post 130 is positioned between the elongate elements 76, with the threads of threaded tip 134 engaged with the threads 77. When the retaining post 130 is tightened within the derotation tube 120, the hexagonal feature 136 will seat against the hexagonal feature 128 of the derotation tube 120 and the tension developed between the engaged threaded tip 134 and the hexagonal feature 136 holds the derotation tube in engagement with the screw assembly 70, and the slots in the side of the engagement feature 124 fit over the rod 112 and prevent rotation of the derotation tube 120 with respect to the screw assembly 70.

Figure 14:
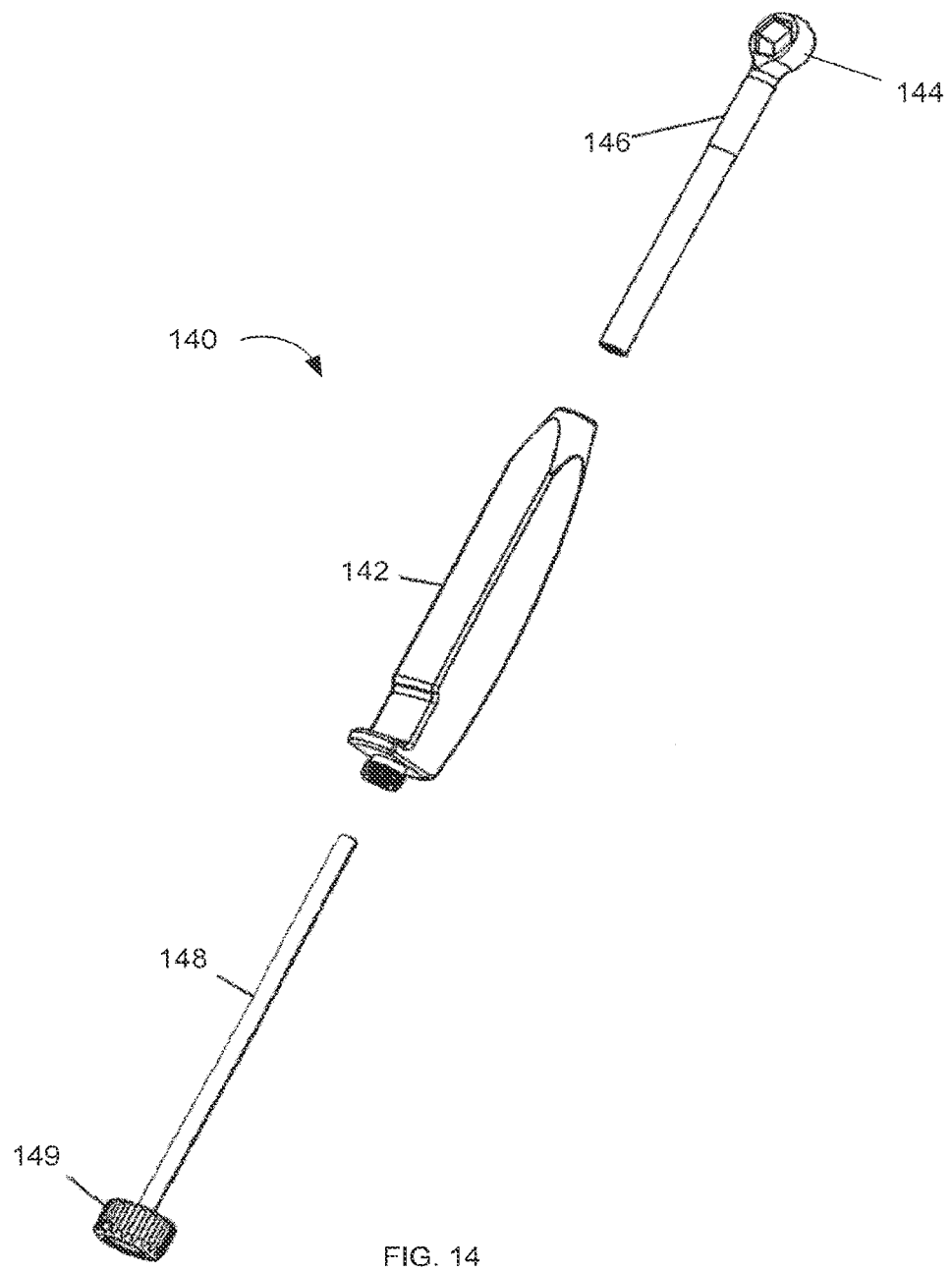
FIG. 14 is an exploded isometric view of the handle of FIG. 13A according to certain embodiments of the present disclosure.

FIG. 14 is an exploded isometric view of the handle 140 of FIG. 13A according to certain embodiments of the present disclosure. The modular handle post 146 is inserted into one end of the modular handle body 142, which has a coupler 144 attached at the other end, with the combination of the modular handle locking nut post 148 and the modular handle locking nut 149 being inserted and threadably coupled to the opposite side of the modular handle body 142. As the modular handle locking nut 149 is advanced, the fixedly attached modular handle locking nut post 148 is driven through the open cannula of the modular handle post 142 and into the open hexagonal opening of coupler 144 and is intended to secure the modular handle assembly 146 to the mating proximal end of the derotation tube 11.

Figure 15A:
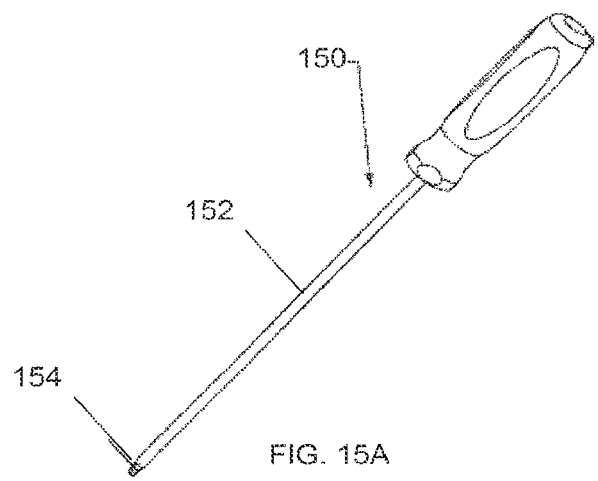
FIG. 15A depicts a hex drive assembly used to tighten the threaded element of the locking cap assembly according to certain embodiments of the present disclosure.

FIG. 15A depicts a hex drive assembly 150 used to tighten the threaded element 104 of the locking cap assembly 100 according to certain embodiments of the present disclosure. The shaft 152 is sized to pass through the bore of retaining post 130 and the drive tip 154 is sized to engage the internal hex feature of the threaded element 104 (not visible).

Figure 15B:
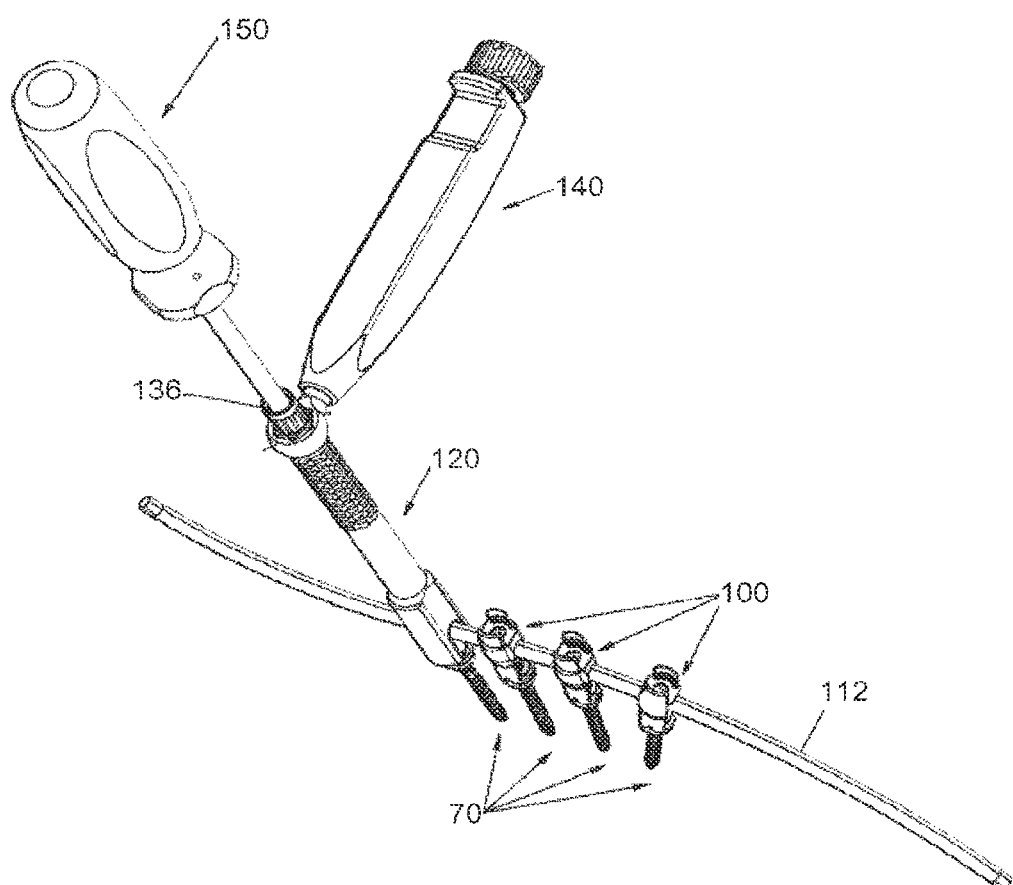
FIG. 15B is an isometric view of the derotation tube of FIG. 13A threadably coupled to one of the screw assemblies of the alignment system of FIG. 11D according to certain embodiments of the present disclosure.

FIG. 15B is an isometric view of the derotation tube 120 of FIG. 13A threadably coupled to one of the screw assemblies 70 of the alignment system 110 of FIG. 11D according to certain embodiments of the present disclosure. A hex driver assembly 150 is inserted through the retaining post receiving end 136. The threaded element 104 is segmentally tightened to the rod 112 by using the hex driver assembly 150. More specifically, the hex tip 154 of the hex driver assembly 150 engages the female hex of the threaded element 104 within the locking cap assembly 100. Handle 140 is attached to derotation tube 120 to prevent the tightening torque from twisting the screw assembly 70. Tightening the locking cap assembly 100 will, as tightened, forces the rod 112 down the U-shaped channel of the housing 72 as described in FIGS. 12A-12B.

Figure 16:
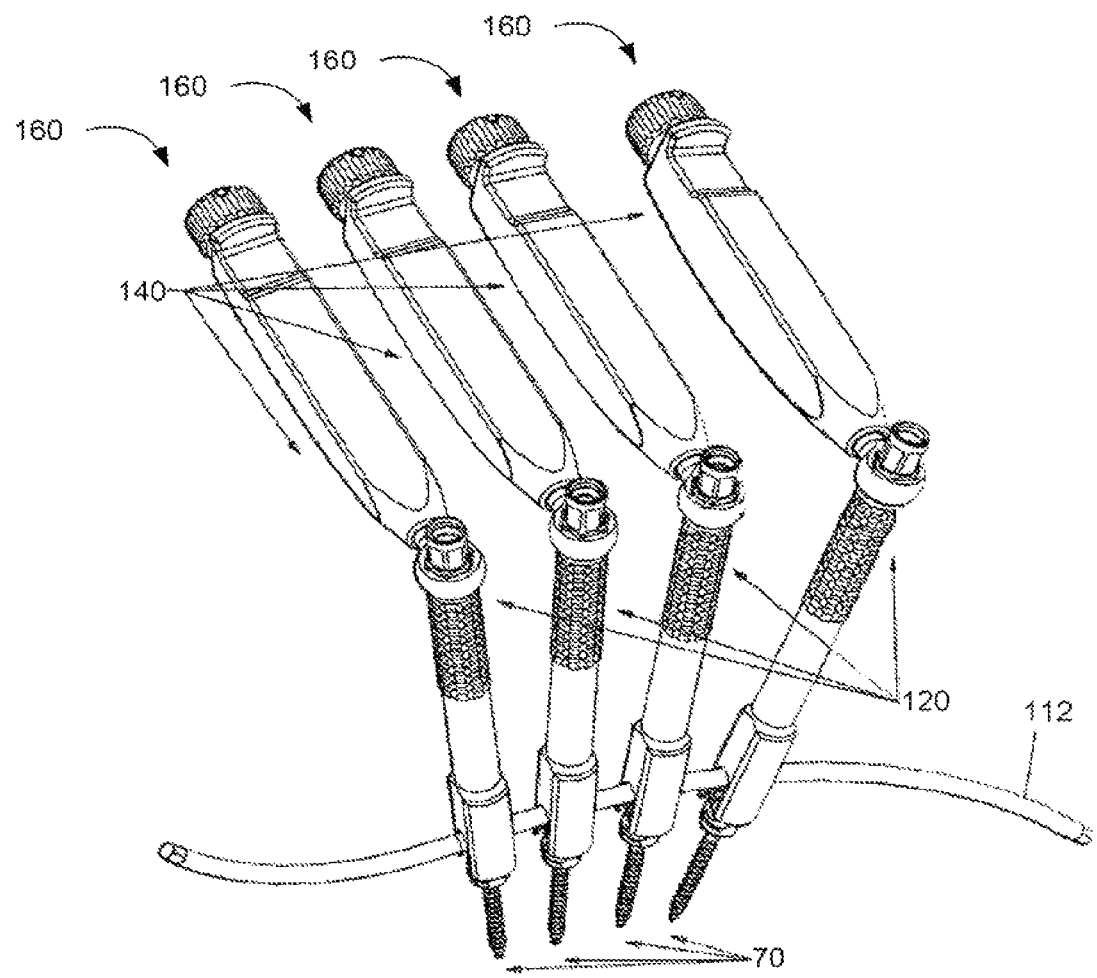
FIG. 16 is an isometric view of multiple derotation assemblies according to certain embodiments of the present disclosure.

FIG. 16 is an isometric view of multiple derotation assemblies 160 according to certain embodiments of the present disclosure. The derotation assemblies 160 are coupled to rod 112.

Figure 17A:
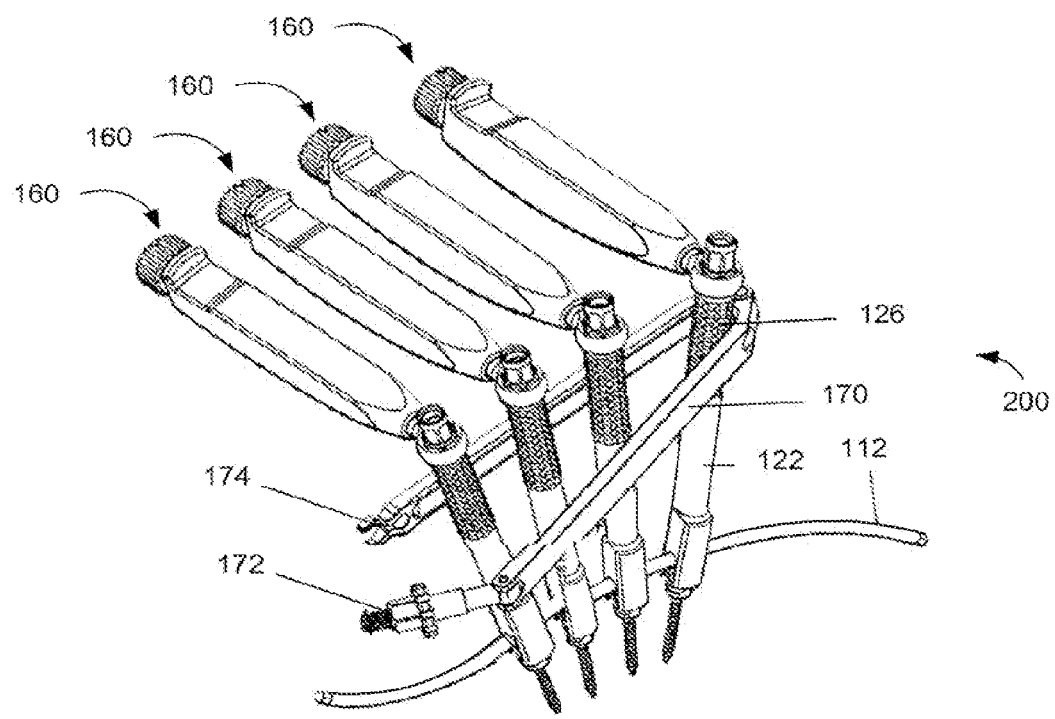
FIG. 17A is an isometric view of a lateral construct assembly according to certain embodiments of the present disclosure.

FIG. 17A is an isometric view of the lateral construct assembly 200 according to certain embodiments of the present disclosure. The lateral construct assembly 200 is formed of the multiple derotation assemblies 160 of FIG. 16 with the addition of a retaining clip assembly 170. The retaining clip assembly 170 is sized to fit around the derotation tube body 122 and engage the knurled surfaces 126 of each of the derotation tubes 120. Once the retaining clip bolt 172 is engaged with the retaining clip nut 174 and tightened, the set of derotation tubes are constrained from translating or rotating with respect to each other. In certain embodiments, more than one retaining clip assembly 170 is installed.

Figure 17B:
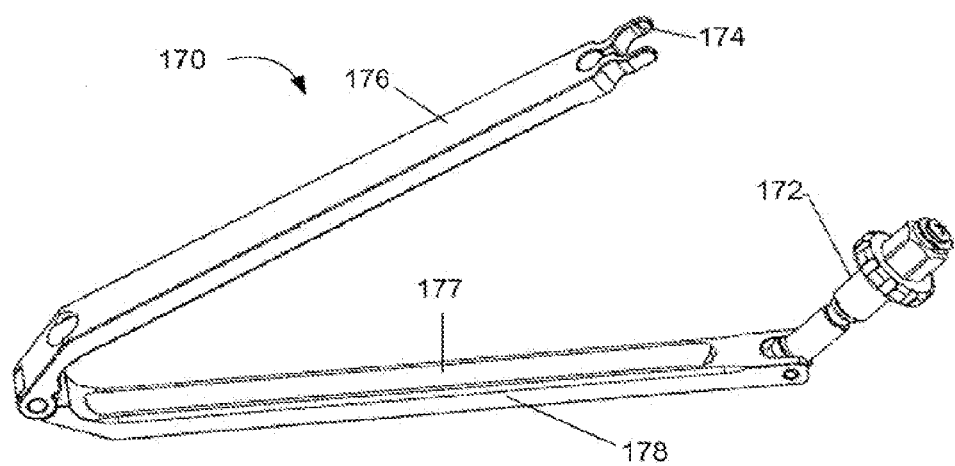
FIG. 17B is an isometric view of a retaining clip assembly according to certain embodiments of the present disclosure.

FIG. 17B is an isometric view of a retaining clip assembly 170 according to certain embodiments of the present disclosure. The retaining clip assembly 170 has two arms 176 and 178 that are, in this embodiment, hingedly connected at one end and have a threaded retaining feature comprising a retaining clip bolt 172 and a retaining clip nut 174 coupled to arms 178 and 176, respectively. When the arms are closed and the retaining clip bolt 172 is engaged with the retaining clip nut 174, tightening the retaining clip bolt 172 draws the arms 176 and 178 closer together. Each arm has a compressible pad 177 disposed on the surface facing the other arm. When the retaining clip assembly 170 is engaged around the knurled surfaces 126 of derotation tubes 120, these compressible pads 177 are in contact with the knurled surfaces 126 and provide a non-slip engagement that resists the derotation tube 120 from turning or sliding with respect to the retaining clip assembly 170.

Figure 18A:
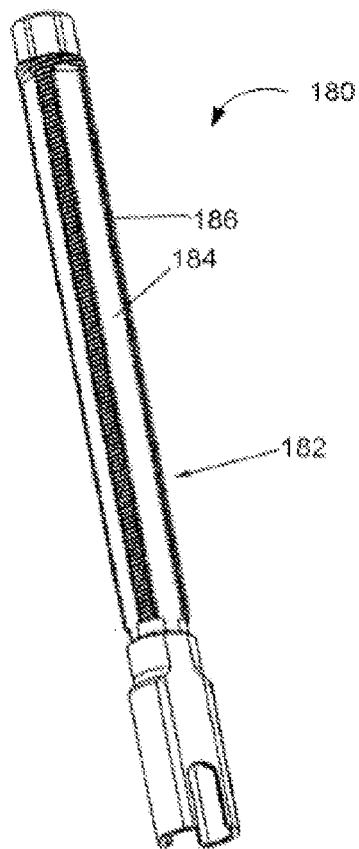
FIGS. 18A and 18B depict the components of another embodiment of a derotation tube according to certain embodiments of the present disclosure.
Figure 18B:
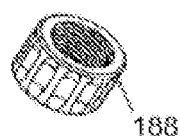

FIGS. 18A and 18B depict the components of another embodiment of a derotation tube 180 according to certain embodiments of the present disclosure. The derotation tube is similar to the derotation tube 120 but with body 182 having a plurality of flats 184 arranged around the circumference of the body 182. In the embodiment of FIG. 18A, there are four flats 184 evenly spaced around the circumference of the body 182. In certain embodiments, there are more than four flats 184. In certain embodiments, there are six flats 184. In certain embodiments, there are less than four flats 184. In certain embodiments, there are only two flats 184. In certain embodiments, there is only a single flat 184. The body also comprises an interrupted series of threads 186 that are aligned across the flats 184.

FIG. 18B depicts a locking nut 188 sided and configured to engage the interrupted threads 186 of derotation tube 182. In certain embodiments, the locking nut 188 is knurled on the outside to improve the grip by the surgeon.

Figure 18C:
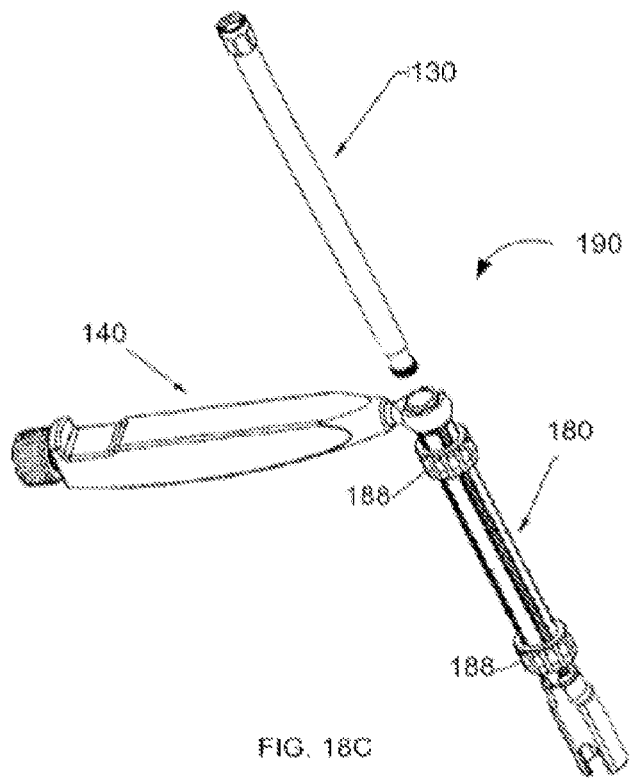
FIG. 18C is an exploded isometric view of a derotation assembly according to certain embodiments of the present disclosure.

FIG. 18C is an exploded isometric view of a derotation assembly according to certain embodiments of the present disclosure. Two locking nuts 188 are engaged with the interrupted threads 186 and positioned towards the distal and proximal ends of derotation tube 180. The same retaining post 130 and handle 140 of FIG. 11A are used with derotation tube 180. Together, the derotation tube 180, retaining post 130, and handle 140 form a derotation assembly 190.

Figure 18D:
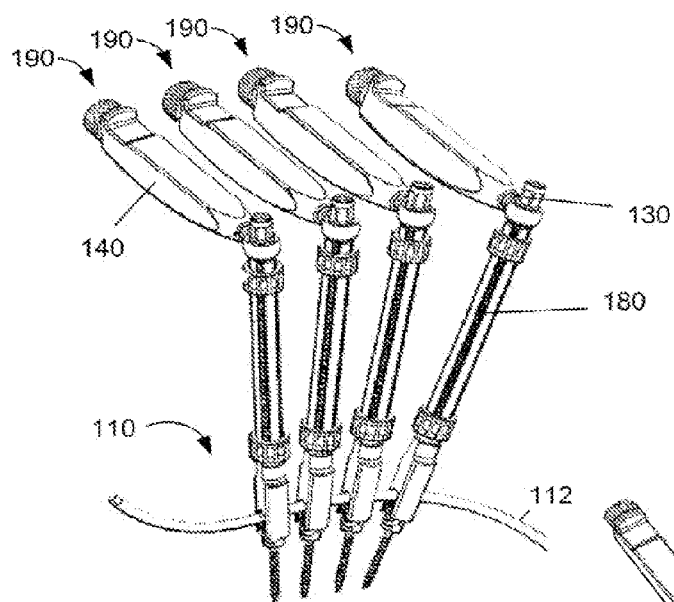
FIGS. 18D-18F depict a lateral construct assembly incorporating multiple derotation assemblies of FIG. 18C and a retaining clip assembly of FIG. 17B according to certain embodiments of the present disclosure.
Figure 18E:
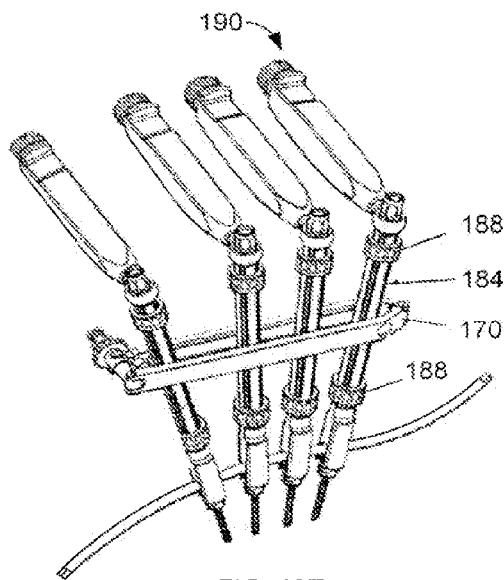
Figure 18F:
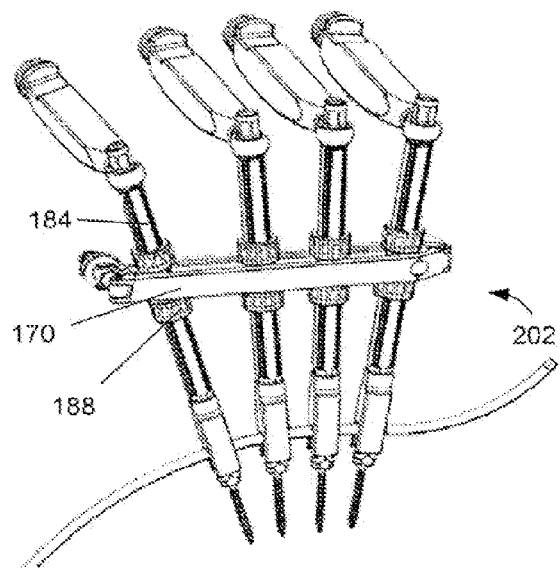

FIGS. 18D-18F depict a lateral construct assembly 202 incorporating multiple derotation assemblies 190 of FIG. 18C and the retaining clip assembly 170 of FIG. 17B installed according to certain embodiments of the present disclosure. FIG. 18A is an isometric view of multiple derotation assemblies 190 coupled to rod 112 FIG. 18E depicts the multiple derotation assemblies 190 with a retaining clip assembly 170 attached between the two locking nuts 188 on each derotation tube 180. The compressible surfaces 177 of the retaining clip assembly 170 are in contact with the flats 184, thereby preventing rotation of the derotation tubes 180 with respect to the retaining clip assembly 170. In certain embodiments, more than one retaining clip assembly 170 is installed. In certain embodiments, more than two locking nuts 188 are installed on at least one derotation tube 180.

FIG. 18F depicts the configuration of the multiple derotation assemblies 190 after the locking nuts 188 have been relocated to contact the retaining clip assembly 170. Together, the multiple derotation assemblies 190 and retaining clip assembly 170 form a lateral construct assembly 202. This embodiment of a lateral construct assembly 202 provides the translation and rotation resistance of the lateral construct assembly 200 of FIG. 17A with the additional constraint that the retaining clip assembly 170 is restrained from sliding in the distal or proximal directions along any of the derotation tubes 180.

Figure 19:
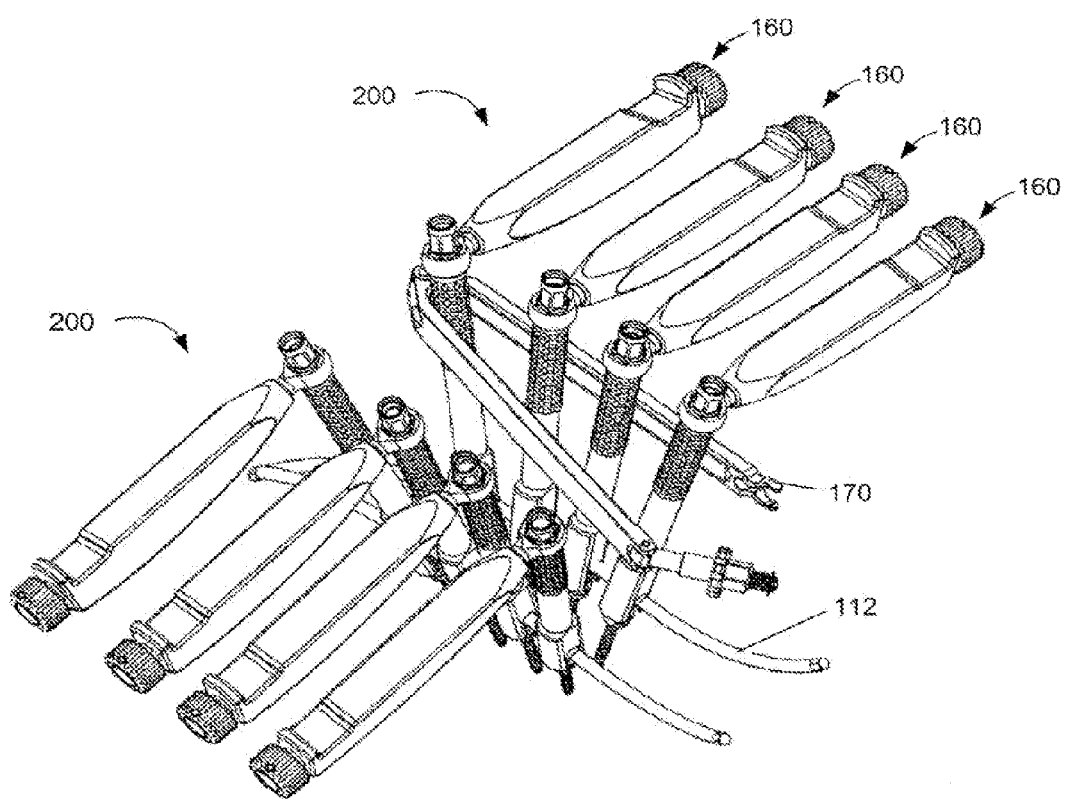
FIG. 19 depicts two lateral construct assemblies arranged on the left and right sides of a spinal column according to certain embodiments of the present disclosure.

FIG. 19 depicts two lateral construct assemblies 200 such as would be arranged on the left and right sides of a spinal column (not shown) according to certain embodiments of the present disclosure. A retaining clip assembly 170 has been placed but not yet tightened around one of the lateral construct assemblies 200.

Figure 20:
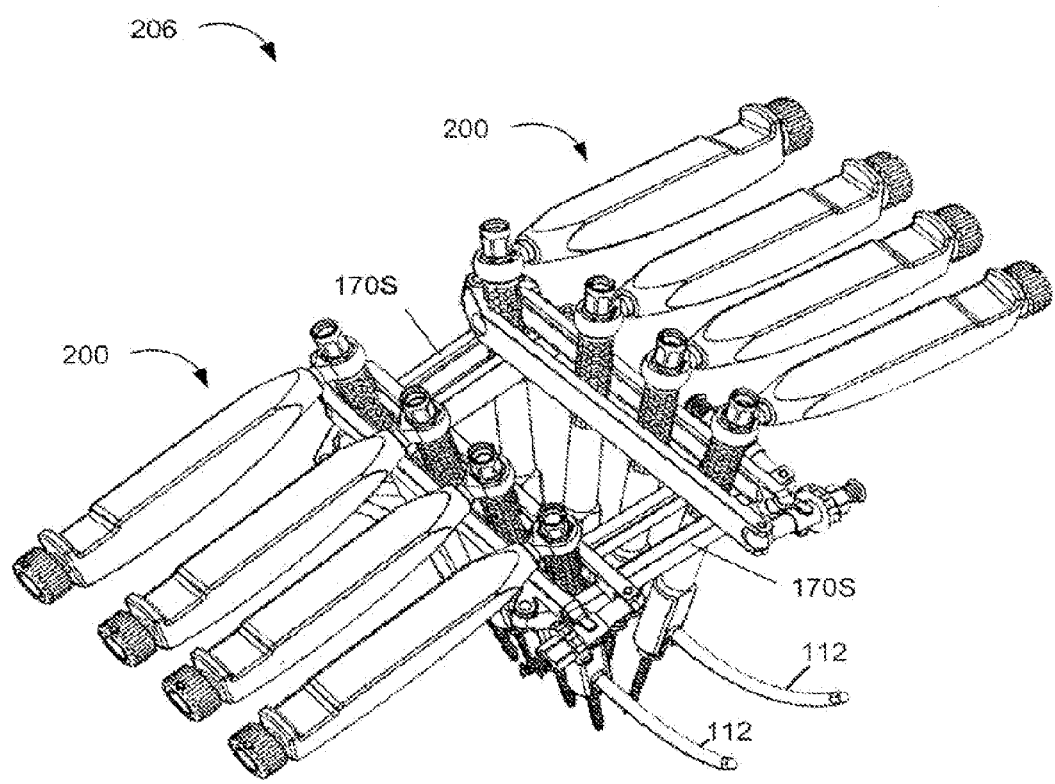
FIG. 20 depicts two lateral construct assemblies joined by two retaining clip assemblies to form a derotation cluster according to certain embodiments of the present disclosure.

FIG. 20 depicts two lateral construct assemblies 200 joined by two retaining clip assemblies 170S to form a derotation cluster 206 according to certain embodiments of the present disclosure. In the embodiment of FIG. 20, a retaining clip assembly 170 has been installed over the proximal end of the knurled region of derotation tubes 120 and tightened. A second pair of short retaining clip assemblies 170S have been installed between the end derotation tubes 120 of the two lateral construct assemblies 200 across the distal portion of the knurled region of derotation tubes 120, binding the two lateral construct assemblies 200 into a single rigid derotation cluster 206.

The derotation cluster 206 can be used by the surgeon to modify the curvature of the spine, e.g. alignment in the transverse plane, as well as rotation in the coronal and sagittal planes. In certain methods of alignment, the rod 112 is rotated using rod gripper (not shown) or a hex wrench (not shown) coupled to the hex ends 112A. In certain methods, one or more of the locking screw assemblies 100 are tightened to retain the coronal and sagittal alignment while the curvature of the spine is adjusted. Unilateral depression of the vertebral body using a derotation cluster 206 creates a lordosis in the spine, whereas lifting the entire derotation cluster 206 will enhance kyphosis. In certain embodiments, additional derotation assemblies 160 are used to provide additional points of manipulation or restraint of one or both of the rods 112. In certain methods, after the derotational maneuver has been completed, each locking screw assembly 100 is slowly tightened incrementally along the construct assemblies 200 to reduce the spine to the rods 112. If no further manipulation is required, the locking cap assemblies 100 can be fully tightened to lock the housings 72 to the screw 40 in the current orientation, and the tops of the elongated elements 76 can be broken off at the grooves 79 shown in FIG. 6B.

Figures 21A, 21B:
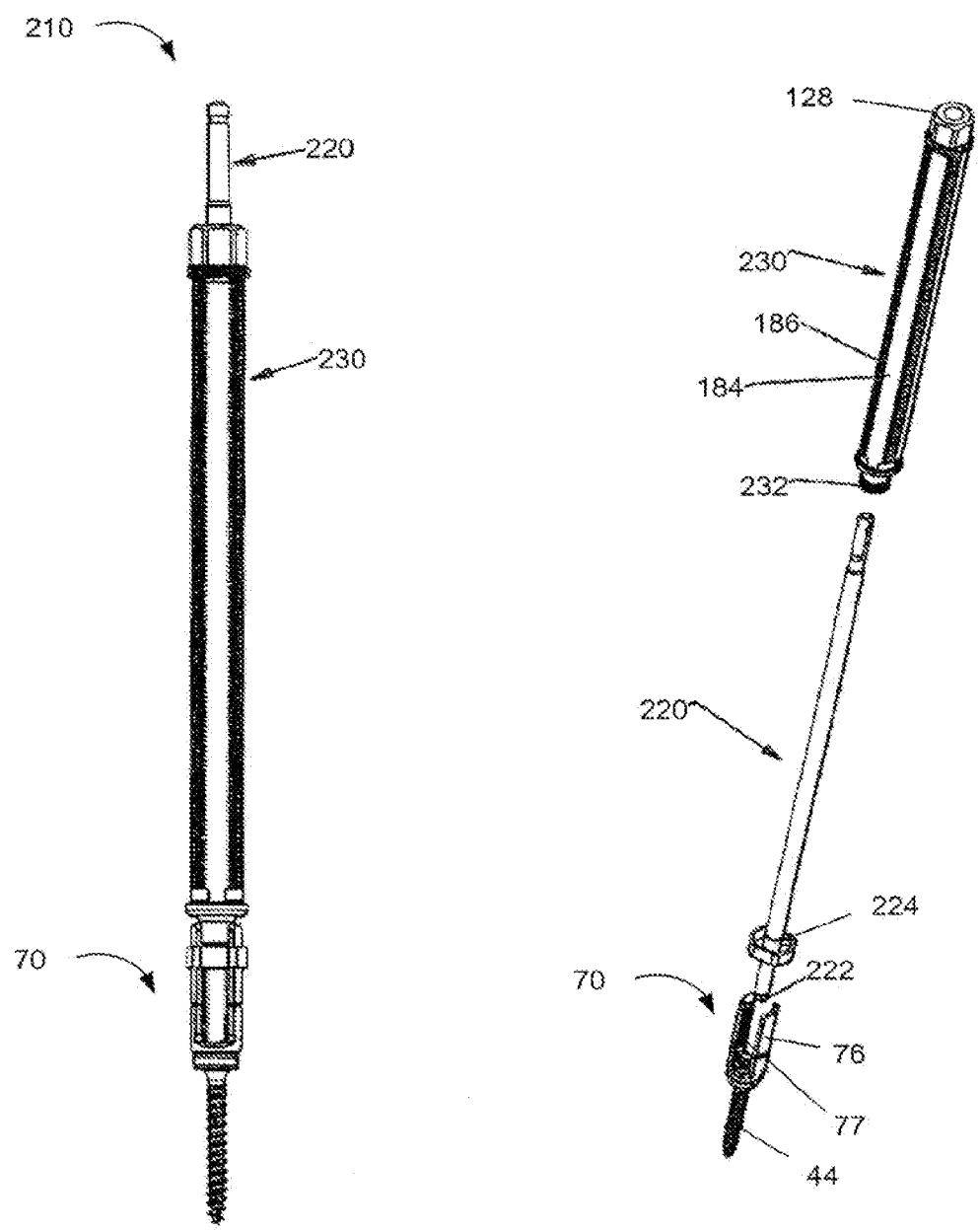
FIGS. 21A-21C depict a derotation sleeve assembly according to certain embodiments of the present disclosure.
Figure 21C:
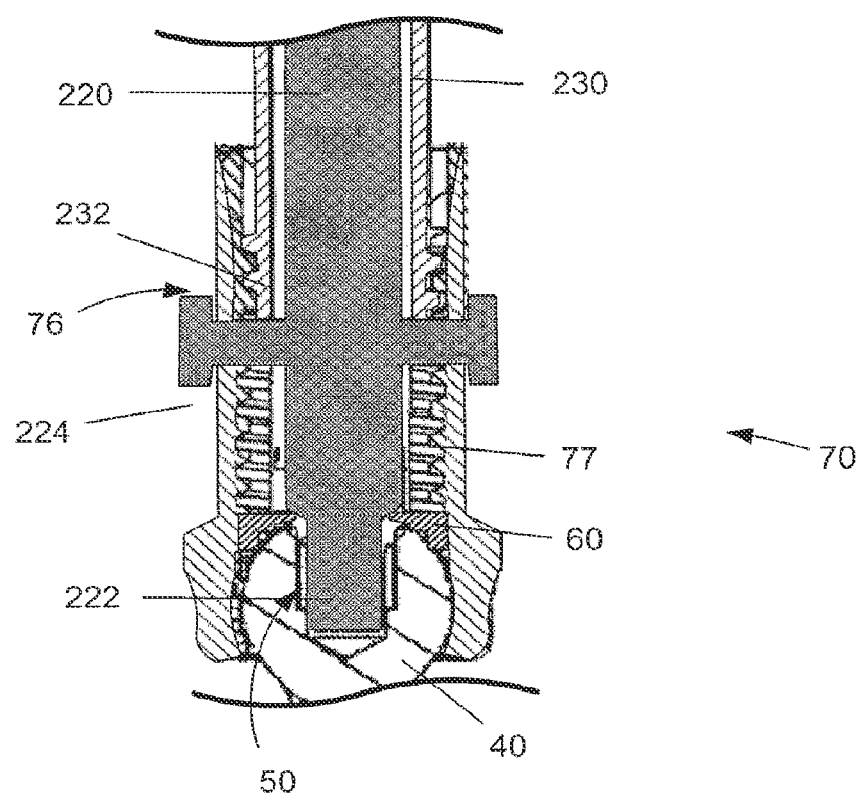

FIGS. 21A-21C depict a derotation sleeve assembly 210 according to certain embodiments of the present disclosure. FIGS. 21A and 21B depict an assembled side view and an exploded isometric view, respectively, of a derotation sleeve assembly 210. The derotation sleeve assembly 210 includes a restraint shaft 220 and a restraint sleeve 230. The restraint shaft 220 has a hex tip 222 that is configured to engage the hexagonal recess 50 of screw 40 and a collar 224 that is configured to slide over the elongated elements 76 of housing 72, thereby centering the restraint shaft 220. In certain embodiments, a polyaxial screw (not shown) replaces the screw 70. The restraint sleeve 230 is similar to the derotation tube 180 in that it has the same flats 184 and interrupted threads 186 as well as a hexagonal feature 128, with the addition of a threaded tip 232. In use, the restraint shaft is positioned above the screw assembly 70 and advanced with the collar 224 sliding over the elongated elements 76 until the hex tip 22 engages the recess 50 of the screw assembly 70. The restraint sleeve 230 is then placed over the restraint shaft 220 and advanced until the threaded tip 232 reaches the threads 77 of the elongated elements 76, whereupon the restraint sleeve 230 is rotated so that the threaded tip 232 engages the threads 77. In certain embodiments, the restraint shaft 220 and the restraint sleeve 230 are configured such that the hex tip 222 is forced into the hexagonal recess 50 as the restraint sleeve 230 advances in the distal direction. When the restraint sleeve 230 is tightened, the threaded portion 44 of the screw assembly 70 is forced to remain in line with the restraint shaft 220 and restraint sleeve 230 to form a derotation sleeve assembly 210. In certain embodiments, the derotation sleeve assembly 210 is used to accomplish derotation of one or more vertebra without use of a rod 112.

FIG. 21C is an enlarged cross-section of the engagement of the restraint shaft 220 and restraint sleeve 230 with screw assembly 70. Hex tip 222 is engaged in the recess 50 of the screw 40. The collar 224 surrounds the elongated elements 76. The threaded tip 232 is engaged with the threads 77 of the elongated elements 76 and is pressed against the collar 224 thereby pressing the hex tip 222 in recess 50 which thereby placing the housing 72 in tension against the screw head 40. In this configuration, the restraint shaft 220 is forced into alignment with the screw 40, and therefore restraint sleeve is therefore also aligned with screw 40.

Figure 22:
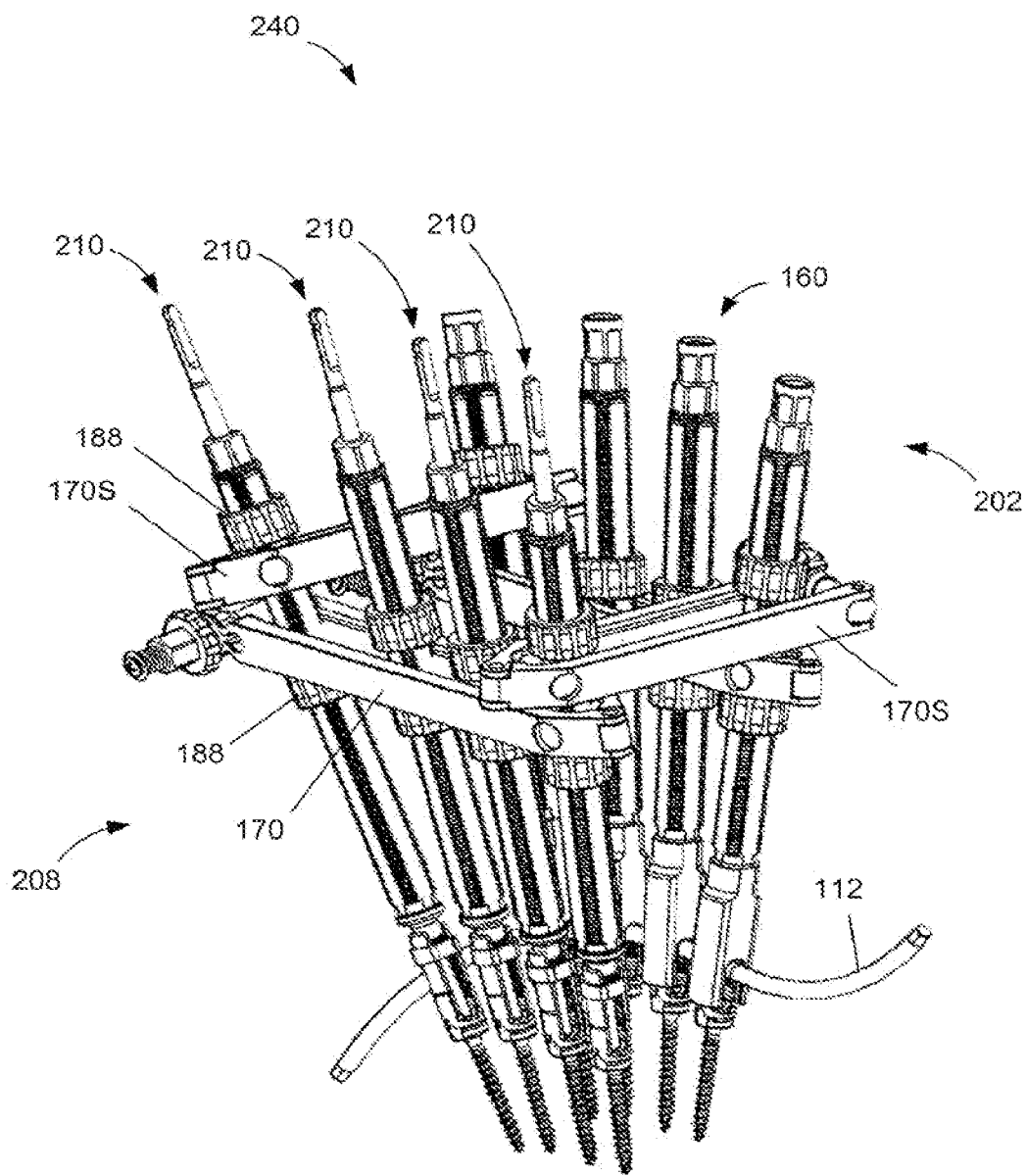
FIG. 22 depicts another derotation cluster formed from a lateral construct assembly and multiple derotation sleeve assemblies according to certain embodiments of the present disclosure.

FIG. 22 depicts another derotation cluster 240 formed from a lateral construct assembly 202 and multiple derotation sleeve assemblies 210 according to certain embodiments of the present disclosure. The lateral construct assembly 202 includes, in this embodiment, four derotation assemblies 160 with two locking nuts 188 each. The multiple derotation sleeve assemblies 210 have been coupled together with a retaining clip assembly 170 to form a lateral construct assembly 208. The lateral construct assemblies 202 and 208 have then been coupled together by a pair of retaining clip assemblies 170S connected across the derotation assembly 160 and derotation sleeve assembly 210 at each end of the group, thereby forming the derotation cluster 240. In this embodiment, the retaining clip assemblies 170S were placed adjacent to the retaining clip assemblies 170 of the two lateral constructs, and the locking nuts 188 were then tightened so as to capture both retaining clip assemblies 170, 170S between them. In other embodiments, three locking nuts are installed on the end derotation assemblies 160 and derotation sleeve assemblies 210 so as to separately lock the two retaining clips 170 and 170S to the center nut. In other embodiments, four locking nuts are installed on the end derotation assemblies 160 and derotation sleeve assemblies 210 so as to separately lock the two retaining clips 170 and 170S between pairs of locking nuts 188.

FIGS. 23A-23B are perspective views of a polyaxial screw and cap according to certain embodiments of the present disclosure. FIG. 23A depicts a screw 310 with a threaded portion 314 and a spherical head 312 that does not have the flats 48 but is otherwise, in certain embodiments, to the uniplanar screw 40 of FIGS. 7A-7B. FIG. 23B depicts a cap 320 that lacks the ears 66 while otherwise, in certain embodiments, similar to cap 60 of FIGS. 5A-5C.

FIGS. 23C-23D are front and side views of the polyaxial screw assembly 300 according to certain embodiments of the present disclosure. In FIGS. 23C and 23D, the polyaxial screw 310 and cap 320 have been assembled with the housing 72 and pins 80 (not visible) to form a polyaxial screw assembly 300. It can be seen that the range of angular displacement 330 of the threaded portion 314 with respect to the housing 72 is uniform in all directions.

Figure 24A:
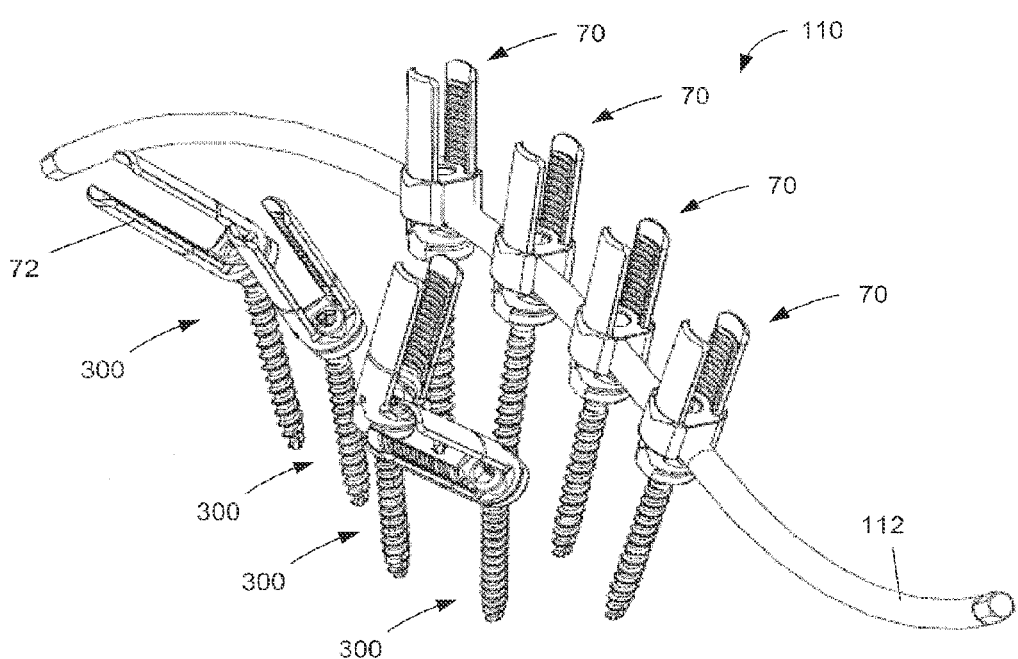
FIGS. 24A-24C depict the insertion of a second rod using the derotation cluster of FIG. 22 according to certain embodiments of the present disclosure.
Figure 24B:
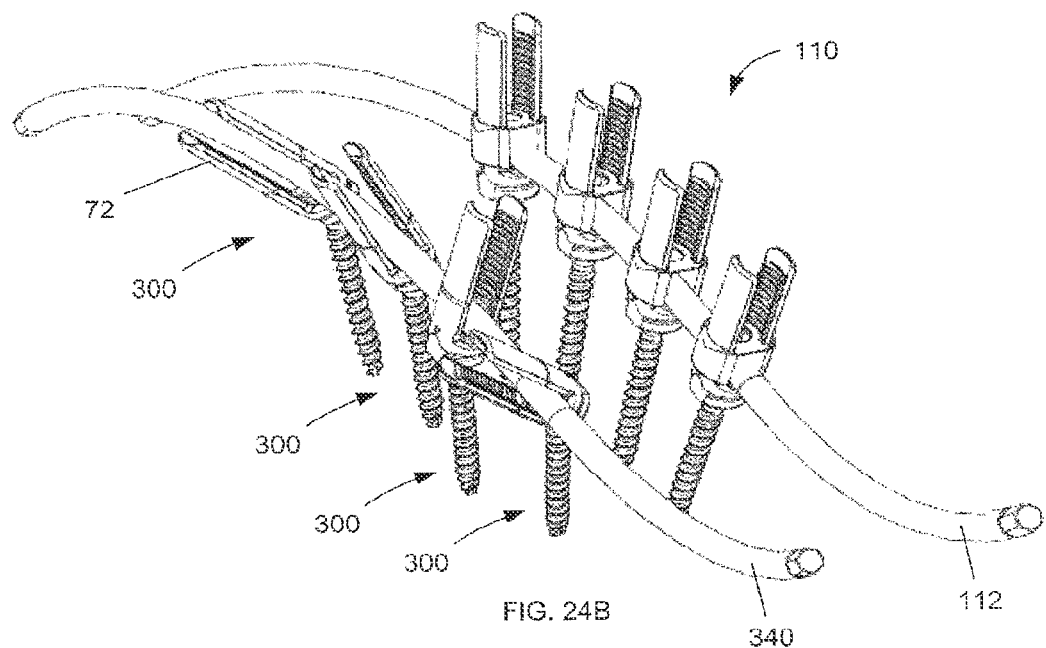
Figure 24C:
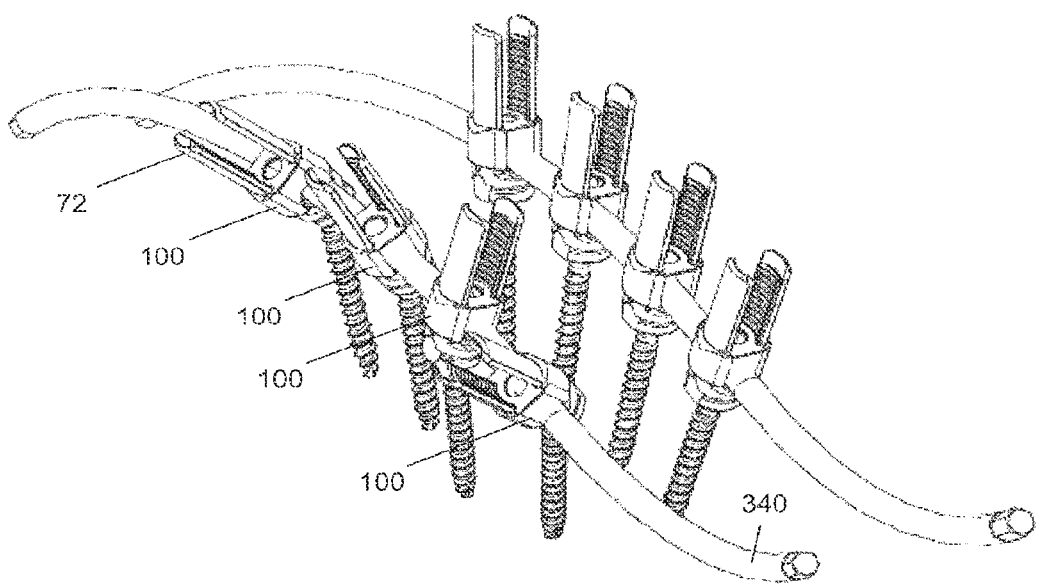

FIGS. 24A-24C depict the insertion of a second rod 340 using the derotation cluster 240 of FIG. 22 according to certain embodiments of the present disclosure. In the embodiments of FIGS. 24A-24C, polyaxial screw assemblies 300 have been used in the derotation sleeve assemblies 210. In FIG. 24A, the retaining clip assemblies 170S and 170 have been removed and the derotation tube assemblies 160 have also been removed from the uniplanar screw assemblies 70, leaving an alignment system 110 similar to that shown in FIG. 11D. Once the locking screw assemblies 100 are tightened, which can be accomplished before the derotation tube assemblies 160 are removed, the patient's spinal vertebrae will be held in place while the second rod 340 is inserted. Additionally in FIG. 24A, the retaining posts of the derotation assemblies 160 have been unscrewed and removed from the derotation tubes 120 and the derotation tubes 120 pulled up and off the polyaxial screw assemblies 300. The housings 72 of the polyaxial screw assemblies 300 are free to rotate and have been individually repositioned such that the U-shaped saddles of the housings 72 are aligned.

In FIG. 24B, the second rod 340 has been placed in the pre-aligned housings 72 of the polyaxial screw assemblies 300. Rod 340 is, in this embodiment, generally similar in shape to the first rod 112. The use of two rods 112, 340 is sometimes preferred to a single rod 112 to provide additional strength and stability in supporting and positioning the patient's spinal vertebrae.

FIG. 24C depicts the addition of locking screw assemblies 100 to each of the polyaxial screw assemblies 300. The locking screw assemblies 100 are incrementally and sequentially tightened until the rod 340 is seated at the bottom of the U-shaped saddle of housing 72 and secured to the housing 72, which also locks the housing 72 to the screw 310 in the current orientation. The upper portions of the elongated elements 76 can then be broken off above the groove 79 for all screw assemblies 70, 300 and the operation completed.

The disclosed systems and methods of use of screw assemblies, derotation assemblies, lateral constructs, and derotation clusters provide surgeons with the capability to correct spinal deformity in the three primary planes of the human body. These various components and assemblies can be used in multiple combinations and techniques depending on the condition of the patient and the preferences of the surgeon.

The previous description is provided to enable a person of ordinary skill in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. An alignment system comprising:
    a plurality of screw assemblies, each screw assembly comprising:
        a housing comprising a plurality of elongated elements forming a U-shaped saddle that is configured to accept a rod, at least one of the elongated elements comprising threads on a portion of its surface facing another elongated element of the plurality of elongated elements;
        a screw extending into and from the housing, the screw comprising a head and a threaded portion, the threaded portion configured to engage bone;
        a plurality of first tubes configured to couple to the housings of respective screw assemblies and to extend beyond the housings when the first tubes are coupled to the housings, each first tube having an externally threaded segment configured to engage the threads of the at least one of the elongated elements of the respective screw assembly;
    wherein each screw assembly comprises a locking cap assembly comprising:
        a sliding element configured to fit around both elongated elements and to slide along the elongated elements; and
        a threaded element disposed within the sliding element and configured to engage the threads of the at least one elongated element;
    wherein each locking cap assembly is configured to be coupled to the housing of the respective screw assembly so as to capture a rod disposed within the U-shaped saddle of the housing and to displace the rod along the U-shaped saddle as the threaded element is tightened into the housing until the rod is in contact with a bottom of the U-shaped saddle and then fixedly couple the rod to the respective screw assembly.

2. The alignment system of claim 1, further comprising a plurality of restraint shafts, each restraint shaft sized to extend through a respective one of the plurality of first tubes, each restraint shaft configured to engage a pocket on the head of a respective screw of the plurality of screws such that the threaded portion of the screw is held in line with the restraint shaft.

3. The alignment system of claim 2, wherein each restraint shaft has a hex tip and each pocket has a hexagonal recess.

4. The alignment system of claim 2, wherein each restraint shaft has a collar attached to the restraint shaft and configured to slide over and surround the elongated elements of the housing of the respective screw assembly.

5. The alignment system of claim 1, wherein each first tube has a first end, a second end, a first end portion, and at least one flat, the second end being opposite the first end, the first end portion extending from the first end toward the second end and comprising the externally threaded segment, the at least one flat extending along an outer surface of the first tube between the first end and the second end.

6. The alignment system of claim 1, further comprising a retaining clip configured to engage a row of the first tubes and, when engaged with the first tubes, to resist displacement of the first tubes with respect to each other.

7. The alignment system of claim 1, wherein the retaining clip comprises two arms, and each of the two arms comprises a compressible pad disposed on a surface facing the other of the two arms.

8. The alignment system of claim 1, further comprising a plurality of second tubes configured to engage the housings of respective screw assemblies and to extend beyond the housings when the second tubes are engaged with the housings, each second tube having a first end, a second end opposite the first end, and an engagement sleeve attached to the second tube at the first end, the engagement sleeve configured to slide over the elongated elements of the housing of the respective screw assembly, the engagement sleeve having slots that fit over a rod extending through the housing, so as to prevent rotation of the second tube with respect to the respective screw assembly, and wherein the first tubes are sized to extend through the second tubes.

9. The alignment system of claim 8, wherein each second tube has an abutment feature that seats against an abutment feature of a respective first tube when both (i) the respective first tube extends through the second tube and (ii) each of the first tube and the second tube is fully engaged with the housing of the respective screw assembly.

10. The alignment system of claim 9, wherein the abutment feature of the second tube is hexagonal, and the abutment features of the first tube is hexagonal.

11. The alignment system of claim 8, wherein each second tube has at least one flat extending along an outer surface of the second tube between the first end and the second end.

12. The alignment system of claim 8, further comprising a retaining clip configured to engage a row of the second tubes and, when engaged with the second tubes, to resist displacement of the second tubes with respect to each other.

13. The alignment system of claim 8, further comprising at least one handle configured to couple removably to at least one of the plurality of second tubes such that, when coupled, a torque can be applied through the handle to the second tube coupled thereto.

14. The alignment system of claim 13, wherein the handle comprises:
a body having a passage;
a handle post comprising:
a coupler having an open cannula configured to engage the surgical tool; and
a shaft fixedly attached to the coupler, the shaft having a bore that passes into the open cannula of the coupler, the shaft also configured to pass through the passage of the body; and
a locking assembly comprising:
a locking nut; and
a locking nut post fixedly attached to the locking nut and configured to engage the bore of the handle post shaft;
wherein rotating the locking nut relative to the handle post shaft advances the locking nut post through the bore of the shaft of the handle post and into the open cannula of the coupler to secure the handle to the surgical tool.

15. The alignment system of claim 14, wherein the open cannula is hexagonal in shape.

16. The alignment system of claim 1, wherein each screw assembly comprises a cap coupled to the housing and configured to engage the head of the screw such that when the cap is engaged with the screw, the relative angular displacement between the threaded portion and the cap is limited.

17. The alignment system of claim 1, wherein each of the elongated elements of the plurality of elongated elements of each screw assembly comprises threads on a portion of its surface facing another elongated element of the plurality of elongated elements.

18. The alignment system of claim 1, further comprising a rod configured to engage the plurality of screw assemblies by moving laterally into the U-shaped saddles.

19. An alignment system comprising:
a plurality of screw assemblies, each screw assembly comprising:
a housing comprising a plurality of elongated elements forming a U-shaped saddle that is configured to accept a rod, at least one of the elongated elements comprising threads on a portion of its surface facing another elongated element of the plurality of elongated elements;
a screw extending into and from the housing, the screw comprising a head and a threaded portion, the threaded portion configured to engage bone;
a plurality of first tubes configured to couple to the housings of respective screw assemblies and to extend beyond the housings when the first tubes are coupled to the housings, each first tube having an externally threaded segment configured to engage the threads of the at least one of the elongated elements of the respective screw assembly; and
a plurality of second tubes configured to engage the housings of respective screw assemblies and to extend beyond the housings when the second tubes are engaged with the housings, each second tube having a first end, a second end opposite the first end, and an engagement sleeve attached to the second tube at the first end, the engagement sleeve configured to slide over the elongated elements of the housing of the respective screw assembly, the engagement sleeve having slots that fit over a rod extending through the housing, so as to prevent rotation of the second tube with respect to the respective screw assembly, and wherein the first tubes are sized to extend through the second tubes.

20. The alignment system of claim 19, wherein each second tube has an abutment feature that seats against an abutment feature of a respective first tube when both (i) the respective first tube extends through the second tube and (ii) each of the first tube and the second tube is fully engaged with the housing of the respective screw assembly.

21. The alignment system of claim 20, wherein the abutment feature of the second tube is hexagonal, and the abutment features of the first tube is hexagonal.

22. The alignment system of claim 19, wherein each second tube has at least one flat extending along an outer surface of the second tube between the first end and the second end.

23. The alignment system of claim 19, further comprising a retaining clip configured to engage a row of the second tubes and, when engaged with the second tubes, to resist displacement of the second tubes with respect to each other.

24. The alignment system of claim 19, further comprising at least one handle configured to couple removably to at least one of the plurality of second tubes such that, when coupled, a torque can be applied through the handle to the second tube coupled thereto.

25. The alignment system of claim 24, wherein the handle comprises:
  a body having a passage;
  a handle post comprising:
    a coupler having an open cannula configured to engage the surgical tool; and
    a shall fixedly attached to the coupler, the shall having a bore that passes into the open cannula of the coupler, the shaft also configured to pass through the passage of the body; and
  a locking assembly comprising:
    a locking nut; and
    a locking nut post fixedly attached to the locking nut and configured to engage the bore of the handle post shaft;
  wherein rotating the locking nut relative to the handle post shaft advances the locking nut post through the bore of the shaft of the handle post and into the open cannula of the coupler to secure the handle to the surgical tool.

26. The alignment system of claim 25, wherein the open cannula is hexagonal in shape.

27. The alignment system of claim 19, wherein each of the elongated elements of the plurality of elongated elements of each screw assembly comprises threads on a portion of its surface facing another elongated element of the plurality of elongated elements.

28. The alignment system of claim 19, further comprising a rod configured to engage the plurality of screw assemblies by moving laterally into the U-shaped saddles.

* * * * *